(12) United States Patent
Park

(10) Patent No.: US 12,186,019 B2
(45) Date of Patent: Jan. 7, 2025

(54) MECHANICAL INTEGRATION OF COMPONENTS OF WEARABLE DEVICES AND OCULAR HEALTH MONITORING SYSTEM

(71) Applicant: Globe Biomedical, Inc., Riverside, CA (US)

(72) Inventor: Joshua Park, Riverside, CA (US)

(73) Assignee: Globe Biomedical, Inc, Riverside, CA (US)

( * ) Notice: Subject to any disclaimer, the term of this patent is extended or adjusted under 35 U.S.C. 154(b) by 0 days.

(21) Appl. No.: 18/493,116

(22) Filed: Oct. 24, 2023

(65) Prior Publication Data

US 2024/0335112 A1 Oct. 10, 2024

Related U.S. Application Data

(60) Provisional application No. 63/495,052, filed on Apr. 7, 2023.

(51) Int. Cl.
*A61B 3/10* (2006.01)
*A61B 3/02* (2006.01)
(Continued)

(52) U.S. Cl.
CPC ............... *A61B 3/14* (2013.01); *G02C 11/10* (2013.01); *A61B 2560/0252* (2013.01)

(58) Field of Classification Search
CPC ......... A61B 3/02; A61B 3/102; A61B 3/1025; A61B 3/113; A61B 3/1015; A61B 3/1225;
(Continued)

(56) References Cited

U.S. PATENT DOCUMENTS

| 5,812,240 A | 9/1998 | Teraoka et al. |
| 6,019,472 A | 2/2000 | Koester et al. |

(Continued)

FOREIGN PATENT DOCUMENTS

| AU | 2017366730 | 5/2019 |
| AU | 2020100831 | 10/2020 |

(Continued)

OTHER PUBLICATIONS

Babenko et al., "Detection of signs of disease in external photographs of the eyes via deep learning", Nature Biomedical Engineering, Sep. 21, 2021, in 24 pages.

(Continued)

*Primary Examiner* — Dawayne Pinkney
(74) *Attorney, Agent, or Firm* — Knobbe, Martens, Olson & Bear, LLP

(57) ABSTRACT

An eyeglasses frame is disclosed that includes a left rim and a right rim. Each of the left rim and the right rim has a medial side and a temporal side. The temporal side of one of the left rim and the right rim has a lens mounting edge and a blind recess that extends from the lens mounting edge. The eyeglasses frame also includes a camera enclosure that is disposed on a posterior segment of the temporal side of one of the left rim and the right rim. The camera enclosure extends from a first end adjacent to the lens mounting edge to a second end disposed posterior of the posterior segment of the one of the left rim and the right rim. The second end of the camera enclosure has an observation aperture, wherein an image viewing axis disposed through the observation aperture is angled medially and upwardly.

21 Claims, 22 Drawing Sheets

(51) Int. Cl.
*A61B 3/14* (2006.01)
*G02C 11/00* (2006.01)

(58) Field of Classification Search
CPC ......... A61B 3/024; A61F 9/026; G02B 27/01;
G02B 27/017; G02C 5/143; G02C 7/00;
G02C 7/024
USPC ....... 351/205, 200, 206, 209, 210, 221–223,
351/246, 41, 111, 159.01, 159.75–159.77;
381/27; 359/630
See application file for complete search history.

(56) References Cited

U.S. PATENT DOCUMENTS

| | | | |
|---|---|---|---|
| 6,110,110 A | 8/2000 | Dublin, Jr. et al. | |
| 6,997,556 B2 | 2/2006 | Pfleger | |
| 7,488,294 B2 | 2/2009 | Torch | |
| 7,515,054 B2 | 4/2009 | Torch | |
| 7,866,819 B2 | 1/2011 | Tuan | |
| 8,905,541 B2* | 12/2014 | Blum | G02C 1/10 351/158 |
| 8,929,589 B2 | 1/2015 | Publicover et al. | |
| 9,041,787 B2 | 5/2015 | Andersson et al. | |
| 9,298,007 B2 | 3/2016 | Border | |
| 9,532,714 B2 | 1/2017 | Border et al. | |
| 9,532,715 B2 | 1/2017 | Border et al. | |
| 9,545,197 B2 | 1/2017 | Korb et al. | |
| 9,552,517 B2 | 1/2017 | Chang et al. | |
| 9,584,971 B1 | 2/2017 | Guo et al. | |
| 9,596,391 B2 | 3/2017 | Henderek et al. | |
| 9,706,912 B2 | 7/2017 | Copland et al. | |
| 9,710,058 B2 | 7/2017 | Gustafsson et al. | |
| 9,770,169 B2 | 9/2017 | Rickard et al. | |
| 9,795,290 B2 | 10/2017 | Grenon et al. | |
| 9,832,412 B2 | 11/2017 | Burkholz et al. | |
| 9,836,122 B2 | 12/2017 | Border | |
| 9,952,664 B2 | 4/2018 | Border et al. | |
| 9,977,960 B2 | 5/2018 | Gustafsson et al. | |
| 10,016,130 B2 | 7/2018 | Ganesan et al. | |
| 10,045,737 B2 | 8/2018 | Tzieli et al. | |
| 10,188,791 B2 | 1/2019 | Burkholz et al. | |
| 10,277,787 B2 | 4/2019 | Andersson et al. | |
| 10,307,085 B2 | 6/2019 | Sales et al. | |
| 10,310,597 B2 | 6/2019 | Biedert et al. | |
| 10,334,212 B2 | 6/2019 | Yin et al. | |
| 10,368,743 B2 | 8/2019 | Gerrans et al. | |
| 10,467,470 B2 | 11/2019 | Gustafsson et al. | |
| 10,565,446 B2 | 2/2020 | Gustafsson et al. | |
| 10,607,075 B2 | 3/2020 | Gustafsson et al. | |
| 10,617,342 B2 | 4/2020 | Sales et al. | |
| 10,638,169 B2 | 4/2020 | Su et al. | |
| 10,686,972 B2 | 6/2020 | Ronngren | |
| 10,802,585 B2 | 10/2020 | Agaoglu et al. | |
| 10,806,341 B2 | 10/2020 | Rickard et al. | |
| 10,842,430 B1 | 11/2020 | Novelli et al. | |
| 10,887,548 B2 | 1/2021 | Mayer et al. | |
| 11,058,295 B2 | 7/2021 | Okazaki et al. | |
| 11,073,903 B1 | 7/2021 | Ouderkirk et al. | |
| 11,103,122 B2 | 8/2021 | Border | |
| 11,619,814 B1 | 4/2023 | Newcombe et al. | |
| 11,806,078 B1 | 11/2023 | Park et al. | |
| 2002/0113943 A1 | 8/2002 | Trajkovic et al. | |
| 2005/0165321 A1 | 7/2005 | Fischell et al. | |
| 2005/0275714 A1* | 12/2005 | Ishikawa | G02C 11/06 348/14.02 |
| 2007/0055222 A1 | 3/2007 | Hohla et al. | |
| 2009/0203985 A1 | 8/2009 | Ehrecke | |
| 2010/0286498 A1 | 11/2010 | Dacquay et al. | |
| 2011/0279666 A1 | 11/2011 | Strombom et al. | |
| 2012/0238857 A1 | 9/2012 | Wong et al. | |
| 2012/0293773 A1 | 11/2012 | Publicover et al. | |
| 2013/0030257 A1 | 1/2013 | Nakata et al. | |
| 2013/0041245 A1 | 2/2013 | Cerboni | |
| 2013/0128364 A1 | 5/2013 | Wheeler | |
| 2014/0055567 A1 | 2/2014 | Dyer | |
| 2014/0055746 A1 | 2/2014 | Nistico et al. | |
| 2014/0228668 A1 | 8/2014 | Wakizaka et al. | |
| 2015/0206008 A1 | 7/2015 | Border et al. | |
| 2017/0235148 A1* | 8/2017 | Kamakura | G02B 27/0176 359/630 |
| 2018/0235465 A1 | 8/2018 | Calpe et al. | |
| 2019/0167095 A1 | 6/2019 | Krueger | |
| 2020/0359886 A1 | 11/2020 | Azar et al. | |
| 2021/0000341 A1 | 1/2021 | Kuperman | |
| 2021/0186318 A1 | 6/2021 | Yellin et al. | |
| 2021/0247617 A1 | 8/2021 | Kassner et al. | |
| 2021/0275019 A1 | 9/2021 | Rickard et al. | |
| 2021/0282669 A1 | 9/2021 | Borden et al. | |
| 2021/0318558 A1 | 9/2021 | Tzvieli et al. | |
| 2022/0139179 A1 | 5/2022 | Park et al. | |
| 2022/0155860 A1 | 5/2022 | Tzvieli et al. | |
| 2022/0236796 A1 | 7/2022 | Konrad et al. | |
| 2022/0280035 A1 | 9/2022 | Zacharov et al. | |
| 2022/0313077 A1 | 10/2022 | Singh et al. | |

FOREIGN PATENT DOCUMENTS

| | | |
|---|---|---|
| CA | 2824921 | 6/2019 |
| CN | 206381163 | 8/2017 |
| CN | 108919517 | 11/2018 |
| CN | 111714341 | 9/2020 |
| CN | 110262074 | 3/2021 |
| CN | 113589554 | 11/2021 |
| CN | 113749610 | 12/2021 |
| EP | 1241976 | 6/2008 |
| EP | 3514606 | 7/2019 |
| JP | 2008-104628 | 5/2008 |
| JP | 5301815 | 9/2013 |
| JP | 5642945 | 12/2014 |
| JP | 2017-211891 | 11/2017 |
| JP | 6396351 | 9/2018 |
| JP | 6535223 | 6/2019 |
| JP | 2020-517012 | 6/2020 |
| WO | WO 2012/129405 | 9/2012 |
| WO | WO-2016149956 A1 * | 9/2016 |
| WO | WO 2018/202929 | 11/2018 |
| WO | WO 2020/214420 | 10/2020 |
| WO | WO 2021/132978 | 7/2021 |
| WO | WO 2022/094446 | 5/2022 |

OTHER PUBLICATIONS

Babenko et al., "Discovering novel systemic biomarkers in photos of the external eye", Jul. 2022, in 49 pages.
Gulshan et al., "Development and Validation of a Deep Learning Algorithm for Detection of Diabetic Retinopathy in Retinal Fundus Photographs", JAMA, Dec. 13, 2016, vol. 316, No. 22, pp. 2402-2410.
Nelson, "Hyperlipidemia as a Risk Factor for Cardiovascular Disease", Prim Care., Mar. 2013, vol. 40, No. 1, pp. 195-211.

* cited by examiner

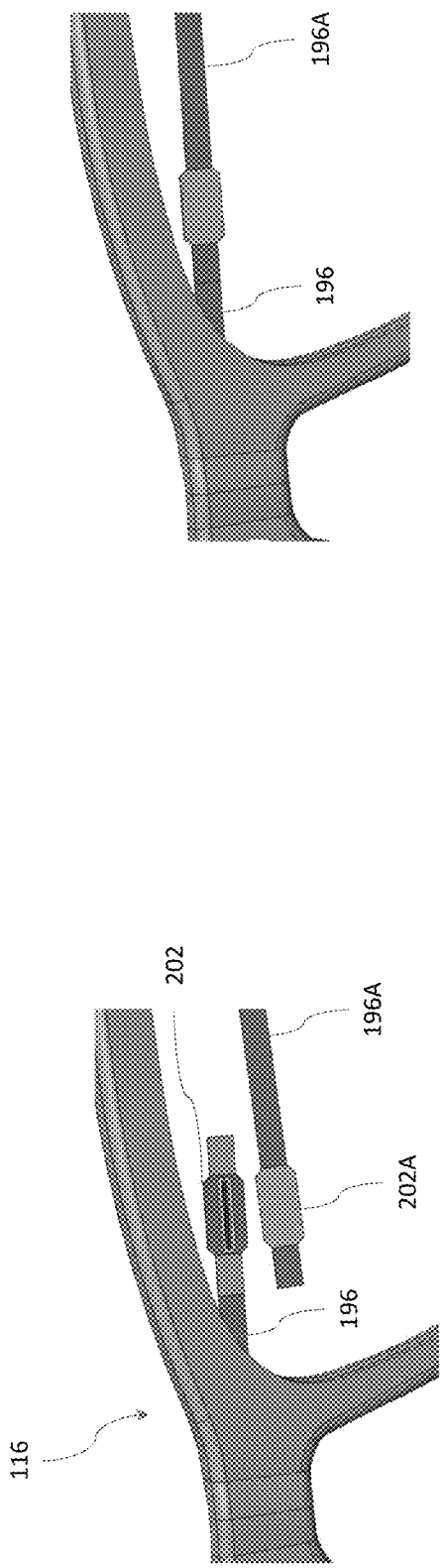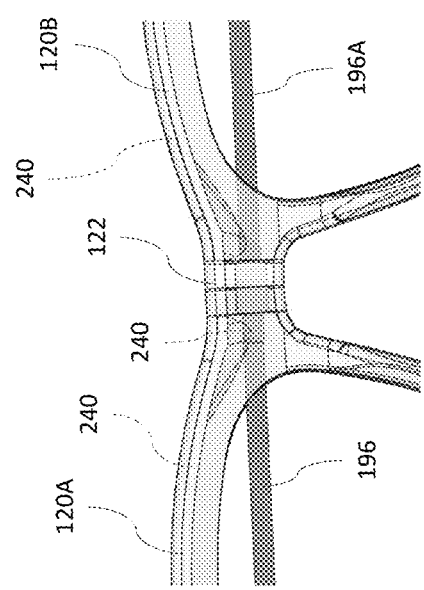
FIG. 18A
FIG. 18B
FIG. 18C

MECHANICAL INTEGRATION OF COMPONENTS OF WEARABLE DEVICES AND OCULAR HEALTH MONITORING SYSTEM

TECHNICAL FIELD

The present disclosure relates generally to wearable devices and ocular health monitoring, and more particularly, to the mechanical integration of components into smart spectacles.

BACKGROUND

Long-standing approaches to monitoring ocular health employ sporadic office-based inspection of the eye. The state of health of an individual's eye and vision is checked in ophthalmologist or optometrist office visits, which may occur yearly, but for many individuals occur less frequently. For less regular patients, optometrist office visits may only be scheduled when the individual notices a degradation in vision. However, many eye conditions develop slowly in an imperceptible manner. Preventable damage to eye structures can occur before the patient notices changes or vision loss.

SUMMARY

Current modes of monitoring eye-health lack sufficient data collection to equip patients and the medical providers to act in a timely manner. For example, patients with progressive eye conditions such as glaucoma may be under regular surveillance, e.g., being professionally examined twice per year. However, this cadence of examinations even if closely adhered to leaves the condition of the patient unknown for long periods of time. While scheduling more frequent patients visits could reduce these data deficiencies, that approach would greatly increase the patient monitoring cost. The inconvenience of office visits leads to poor patient compliance. A more convenient approach to generating more frequent actionable data is needed. Devices and methods for ocular health monitoring that are unobtrusive are needed. Devices and methods that can be integrated into a patient's normal routine are needed.

In one embodiment, an ophthalmic monitoring system is provided that includes an eyeglasses frame, a camera enclosure, and a camera assembly including a camera. The camera may be more generally referred to herein as an image sensor. The image sensor may be said to be housed in an image sensor enclosure. The camera assembly may be referred to herein as an image sensor assembly. The eyeglasses frame has a left rim and a right rim. Each of the left rim and the right rim has an anterior segment, a posterior segment, and a temporal span. The anterior segment can have an anterior lens mounting edge. The posterior segment can have a posterior lens mounting edge. The temporal span can have a u-shaped inner periphery that extends from the anterior segment to the posterior segment, e.g., from the anterior lens mounting edge to the posterior lens mounting edge. The camera enclosure can be disposed on at least one of, e.g., on each of, the posterior segment of the left rim and the posterior segment of the right rim. The camera enclosure is disposed about a space interior to the eyeglasses frame. The space extends from a first end adjacent to the anterior lens mounting edge to a second end disposed posterior of the posterior segment of the left rim and of the right rim. The second end of the space within the camera enclosure has an observation aperture. An image viewing axis is disposed transverse to, e.g., perpendicular to, one or both of the first end and the observation aperture. The viewing axis can be angled medially and at an angle between about 25 degrees and about 40 degrees relative to a vertical plane. The viewing axis can be angled upwardly at an angle between about 10 degrees and about 25 degrees * relative to a horizontal plane. The camera assembly includes a camera disposed in the space interior to the eyeglasses frame adjacent to the observation aperture of the camera enclosure. The camera assembly includes a conductor configured to convey image signals from and control signals to the camera. The conductor extends in the u-shaped inner periphery peripherally of the anterior lens mounting edge and the posterior lens mounting edge.

In another embodiment, an ophthalmic monitoring system is provided that includes an eyeglasses frame, a camera enclosure, and a camera assembly. The eyeglasses frame has a left rim and a right rim. The left rim and the right rim are coupled at a medial portion of the eyeglasses frame. Each of the left rim and the right rim has a u-shaped inner periphery and a lens mounting edge between an anterior surface of an anterior segment of each of the right rim and the left rim and a posterior surface of a posterior segment of each of the right rim and the left rim. The camera enclosure projects along a viewing axis from a temporal span of the posterior segment of one of the left rim and the right rim. The camera enclosure defines an elongate space interior to the eyeglasses frame that extends from an end comprising an observation aperture to another end opposite to the observation aperture. The elongate space is open on a medial side and enclosed by the eyeglasses frame on a lateral side. The observation aperture can be configured such that the viewing axis is angled medially. The observation aperture can be configured such that the viewing axis is angled upwardly. The observation aperture is configured such that the viewing axis is angled medially and upwardly. The camera assembly has a camera and a conductor configured to convey signals between the camera and a processor. The camera is disposed adjacent to the observation aperture. The camera is oriented along the viewing axis to capture images of a lateral side of an eye. The camera also can capture images of tissue surrounding the eye, e.g., medially from a lateral canthus of the eye and from a lower eyelid of the eye to an upper eyelid. In some embodiments, the camera can capture images from a lateral canthus of the eye to a medial portion of a cornea of the eye.

In another embodiment, an eyeglasses frame is provided that includes a left rim and a right rim. Each of the left rim and the right rim has a medial side and a temporal side. The temporal side of one of the left rim and the right rim has a lens mounting edge and a blind recess that extends from the lens mounting edge. The eyeglasses frame also includes a camera enclosure that is disposed on a posterior segment of the temporal side of one of the left rim and the right rim. The camera enclosure extends from a first end adjacent to the lens mounting edge to a second end disposed posterior of the posterior segment of the one of the left rim and the right rim. The second end of the camera enclosure has an observation aperture, wherein an image viewing axis disposed through the observation aperture is angled medially and upwardly.

In another embodiment, a spectacles frame assembly is provided that includes a spectacles frame and a closure. The spectacles frame has a left rim and a right rim. Each of the left rim and the right rim has a medial side, a temporal side, a superior transverse span between the medial side and the temporal side and an inferior transverse span between the medial side and the temporal side. The spectacles frame assembly includes a blind recess that extends into the superior transverse span of one of the left rim and the right rim. The blind recess has a conductor passage configured to receive a conductor (e.g., wires or a flex circuit assembly that has a conductor) configured to convey electrical signals through the superior transverse span. The closure has a superior side configured to be inserted into the blind recess to enclose the conductor passage. The closure has an inferior side configured to engage a superior edge of a lens of a pair of spectacles comprising the spectacles frame.

In another embodiment, a method of assembling spectacles is provided. In the method, a spectacles frame is provided. The spectacles frame has a left rim and a right rim. Each of the left rim and the right rim has a medial side, a temporal side and a superior transverse span between the medial side and the temporal side. The superior transverse span has a blind recess that has a conductor passage disposed therein. A portion of a flex circuit is positioned in the conductor passage. The flex circuit has a conductor configured to convey electrical signals through the superior transverse span. A closure is advanced into the blind recess of the superior transverse span. The closure is secured in the blind recess to enclose the conductor passage.

In another embodiment, a spectacles assembly is provided that has a spectacles frame, a right temple, a left temple, and a hinge assembly. The spectacles frame has a left rim that has one or more mount points, a right rim, and a bridge disposed between the left rim and the right rim. The right temple is coupled with the right rim. The left temple has a blind recess that has a first end of a circuit board disposed therein. The first end of the circuit board has a processor mounted thereon. The circuit board assembly has a second end that has an LED assembly disposed thereon. The hinge assembly connects the left temple to the spectacles frame. The hinge assembly has an axle and a rotatable body. The axle is coupled with the one or more mount points. The rotatable body has a barrel disposed at a first end and disposed around the axle. The rotatable body has a flange at a second end opposite the first end. A temple interface disposed on the rotatable body, e.g., between the flange and the barrel, forms a mechanical connection about a periphery of the blind recess of the left temple. The rotatable body has a translucent portion disposed between the temple interface and the barrel. The rotatable body has a hinge passage disposed through the temple interface. The second end of the circuit board is disposed in the hinge passage and through the temple interface such that the LED assembly is disposed at or adjacent to the translucent portion of the rotatable member. Light from the LED assembly is visible at the translucent portion.

In another embodiment, a spectacles assembly is provided that includes a front frame, a temple, a circuit board, and a hinge assembly. The front frame is configured for mounting lenses thereto and has a hinge mount feature. The temple has an elongate body having a free end and a recess disposed at a fixed end opposite to the free end. The circuit board has a processor mounted thereto disposed in the recess. The hinge assembly connects the temple to the front frame. The hinge assembly has an axle and a rotatable body that has a barrel disposed around the axle. The axle is coupled with the hinge mount feature of the front frame. The rotatable body has a flange disposed opposite to the barrel, a temple interface disposed between the flange and the barrel. The temple interface is configured to mechanically couple the rotatable body to the fixed end of the temple. The rotatable body has a translucent portion disposed between the flange and the barrel. An LED assembly electrically connected to the processor and disposed at or adjacent to the translucent portion such that light from the LED assembly is visible at the translucent portion.

In another embodiment, a spectacles assembly is provided that includes a front frame assembly, a temple, a hinge assembly, and an LED. The front frame is configured for supporting lenses. The front frame has a hinge mount feature. The temple has an elongate body that has a free end and a fixed end opposite to the free end. The hinge assembly connects the temple to the front frame. The hinge assembly has a pivot (e.g., an axle) and a rotatable body. The axle is coupled with or disposed at the hinge mount feature. The rotatable body has a temple interface. The hinge assembly also has a translucent portion. The translucent portion is disposed along a medial side of the hinge assembly. The LED is disposed adjacent to the translucent portion to illuminate the translucent portion within a field of view of a wearer of the spectacles assembly.

In another embodiment, a smart spectacles assembly is provided that includes an eyeglasses frame comprising a left rim and a right rim. A left temple is coupled with the left rim. A right temple is coupled with the right rim. A battery is coupled with the left temple or the right temple. A finger tap sensor is disposed on the smart spectacles assembly operating on current from the battery. The finger tap sensor is configured to generate a signal based on user input comprising a finger tap. The finger tap sensor can comprise an inertial measurement unit. The smart spectacles assembly includes a processor configured to sample the signal generated by the finger tap sensor at a first sampling rate. The processor is configured to detect an initial user input comprising an initial finger tap. The processor can be configured to exclude data corresponding to a harmonic decay period for a first period following detecting the initial user input. The processor can be configured to sample the signal generated by the finger tap sensor after the initial user input, e.g., at a second sampling rate greater than the first sampling rate. The second sampling rate can be operative for a heightened sampling rate period. The processor can be configured to alter an operational parameter of the smart spectacles assembly upon detecting one or more additional user inputs after the harmonic decay period. The processor can be configured to resume sampling at the first sampling rate upon not detecting additional user inputs during the heightened sampling rate period.

In another embodiment, a smart spectacles assembly is provided that includes an spectacles frame, a left temple, and a right temple. The smart spectacles assembly 100 also includes a battery coupled with the left temple or the right temple, a sensor, and a processor. The left temple coupled with a left rim. The right temple is coupled with a right rim. The sensor is disposed on the smart spectacles assembly. The sensor is configured to generate a signal based on user input. The processor is configured to operate on current from the battery. The is also configured to sample the signal generated by the sensor at a first sampling rate. The processor is configured to detect an initial user input. The processor is configured to sample the signal generated by the sensor at a second sampling rate greater than the first sampling rate. The processor can sample the signal at the second sampling rate for a heightened sampling rate period. The heightened sampling rate period can follow the detection of the initial user input. For example, the heightened sampling rate period can immediately follow the detection of the initial user input. The heightened sampling rate period can follow the detection of the initial user input after a pre-defined lag period. The processor is configured to alter an operational parameter of the smart spectacles assembly upon the processor detecting one or more additional user inputs while sampling at the second sampling rate.

In another embodiment, method of controlling a smart spectacles assembly is provided. A signal generated by a sensor configured to detect a user input is sampled at a first sampling rate. An initial user input is detected from the signal generated by the sensor. After a harmonic delay period of the sensor following detecting the initial user input has concluded, the signal generated by the sensor is sampled at a second sampling rate greater than the first sampling rate. If one or more additional user inputs is detected after the harmonic delay period has passed, then an operational parameter of the smart spectacles assembly is altering.

For purposes of summarizing the disclosure, certain aspects, advantages and novel features of several implementations have been described herein. It is to be understood that not necessarily all such advantages are achieved in accordance with any particular implementation of the technology disclosed herein. Thus, the implementations disclosed herein can be implemented or carried out in a manner that achieves or optimizes one advantage or group of advantages as taught herein without necessarily achieving other advantages that can be taught or suggested herein.

BRIEF DESCRIPTION OF THE DRAWINGS

Certain features of this disclosure are described below with reference to the drawings. The illustrated implementations are intended to illustrate, but not to limit, the implementations. Various features of the different disclosed implementations can be combined to form further implementations, which are part of this disclosure.

FIGS. 18A-18C illustrate a step of a method of assembling the flex circuit to provide a conductor between circuit boards disposed at or in the left temple and the right temple.

DETAILED DESCRIPTION

Figure 1:
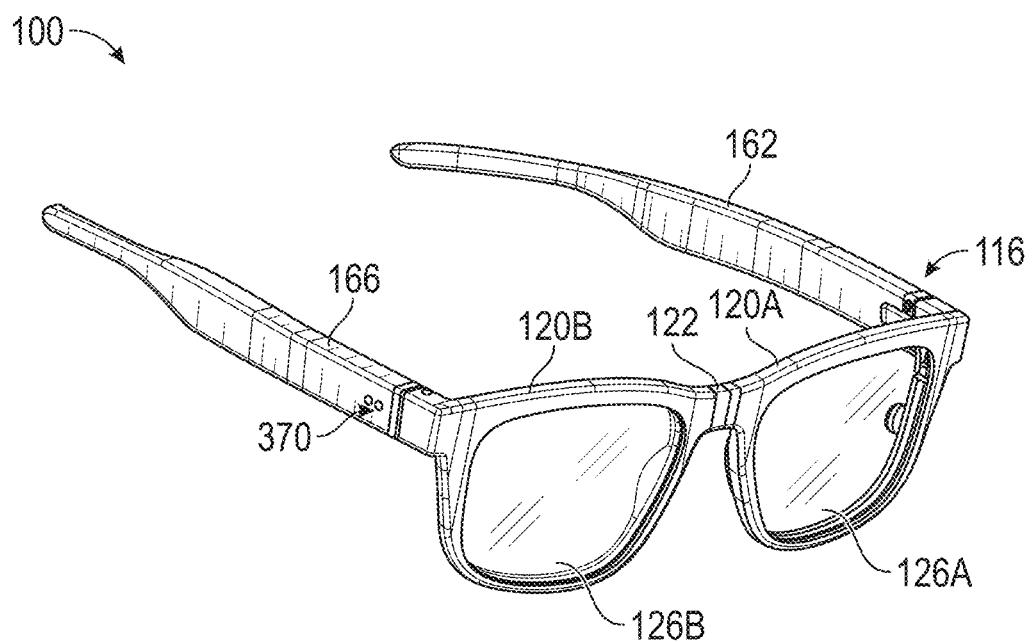
FIG. 1 is a front perspective view of one embodiment of a spectacles assembly to be used in an ophthalmic monitoring system.

Various features and advantages of this disclosure will now be described with reference to the accompanying figures. The following description is merely illustrative in nature and is in no way intended to limit the disclosure, its application, or uses. This disclosure extends beyond the specifically disclosed implementations and/or uses and obvious modifications and equivalents thereof. Thus, it is intended that the scope of this disclosure should not be limited by any particular implementations described below. The features of the illustrated implementations can be modified, combined, removed, and/or substituted as will be apparent to those of ordinary skill in the art upon consideration of the principles disclosed herein. Furthermore, implementations disclosed herein can include several novel features, no single one of which is solely responsible for its desirable attributes, or which is essential to practicing the systems, devices, and/or methods disclosed herein.

The present disclosure describes various implementations of smart spectacles for monitoring ophthalmic conditions, states, and parameters. In certain embodiments, this application is directed to providing for enhanced image capture capabilities for an image sensor or camera to be integrated into a spectacles frame (e.g., eyeglasses frame, eyeglasses, glasses, spectacles frame assembly, etc.). The image sensor or camera is to be unobtrusive such that the smart spectacles closely resemble traditional eyeglasses while providing a wide range of imaging and monitoring functionalities. In certain embodiments, the smart spectacles are configured such that many electronic components are embedded in the spectacles frames. As such, several advantageous configurations for integrating such components in an unobtrusive manner are provided. The spectacles frame are configured for routing conductors, e.g., flex circuits, within channels formed therein. The channels in the spectacles frame can enable conductors, e.g., in flex circuits, to provide wired connection to circuit boards on both sides of the spectacles frame. The channels in the spectacles frame can enable conductors, e.g., in flex circuits, to provide wired connection to circuit boards on an opposite side of the spectacles frame from where a component is located. Such routing can advantageously enable power on either side of the spectacles frame to support processing of electronic component on the same or opposite sides of the spectacles frame. Electrical connection through the spectacles frame, e.g., across an anterior-posterior mid-plane of the frame, can be through glasses features that are not visibly different from traditional eyeglasses. In some embodiments, the smart spectacles are configured to provide a visible user interface through a structural component without requiring projection of graphical images into the field of view. A component configured to convey device state to the user can be provided at a periphery or a rim or frame component or in a peripheral vision area of the smart spectacles.

FIG. 1 illustrates a component of an ophthalmic monitoring system, i.e., a smart spectacles assembly 100. The smart spectacles assembly 100 can be integrated into an ophthalmic monitoring system 78, illustrated in FIG. 1A, that can include a combination of patient worn components and external computing system. The external computing systems can be accessed by a communications interface 88 embedded in the smart spectacles assembly 100. The communications interface 88 can communicate with a wireless data transfer technology, e.g., a Wi-Fi and/or Bluetooth device 86 or other wireless transmitter. The smart spectacles assembly 100 can be operated and powered by a battery 82 that can be charged periodically. The battery 82 enables the smart spectacles assembly 100, and hence the embedded systems therein, to be worn by a person without being tethered to a wired power connection.

The smart spectacles assembly 100 can include a microcontroller unit (MCU) having a processor 278 that cooperates with a power supply module 84 that regulates and delivers the needed electrical power thereto. The rechargeable battery 82 provides electrical energy to the power supply module 84. The specific type and capacity of battery may be selected based upon the overall power consumption by the entirety of the smart spectacles assembly 100 over a desired operational duration. The battery 82 with the requisite power capacity to operate the microcontroller unit and the processor 278 and the other electrical components of the system has a significant physical footprint. The battery 82 can be located within the right temple 166 opposite a circuit board 274 to which the processor 278 is coupled. Of course, the battery 82 could be located on the left temple 162 in other configurations.

As the embedded system operates over time, the reserve power in the battery 82 will be drained, and so in order to continue functioning, it may need to be recharged. In this regard, the system 78 also incorporates a charging circuit 90 that can connect to an external power source. The external power source can be a charge device in the form of a cable assembly primarily for supplying power to the battery 82 or a dedicated cradle or base station that provide for charging and that houses a transceiver for communicating with the Wi-Fi and/or Bluetooth device 86. The Wi-Fi and/or Bluetooth device 86 can communicate with a separate device such as a router or modem with access to the Internet and thereby to a remote computing device for data processing and/or storage, e.g., a cloud 80 The interface for making this connection may be charge conductors 370 exposed on a side surface of one or both of the left temple 162 and the right temple 166. In other approaches, a Universal Serial Bus (USB) port could be provided, which has a dedicated pinout for a power supply. As will be described in further detail below, embodiments of the present disclosure contemplate data transfer to and from the smart spectacles assembly 100. If provided, a USB could be used for both charging and data transfer from the smart spectacles assembly 100 on the left temple 162 or the right temple 166. If USB is employed, microUSB may be utilized to reduce the form factor. In additional embodiments other structure and methods can be employed for charging the battery 82. For example, wireless inductive charging can be employed.

Figure 1A:
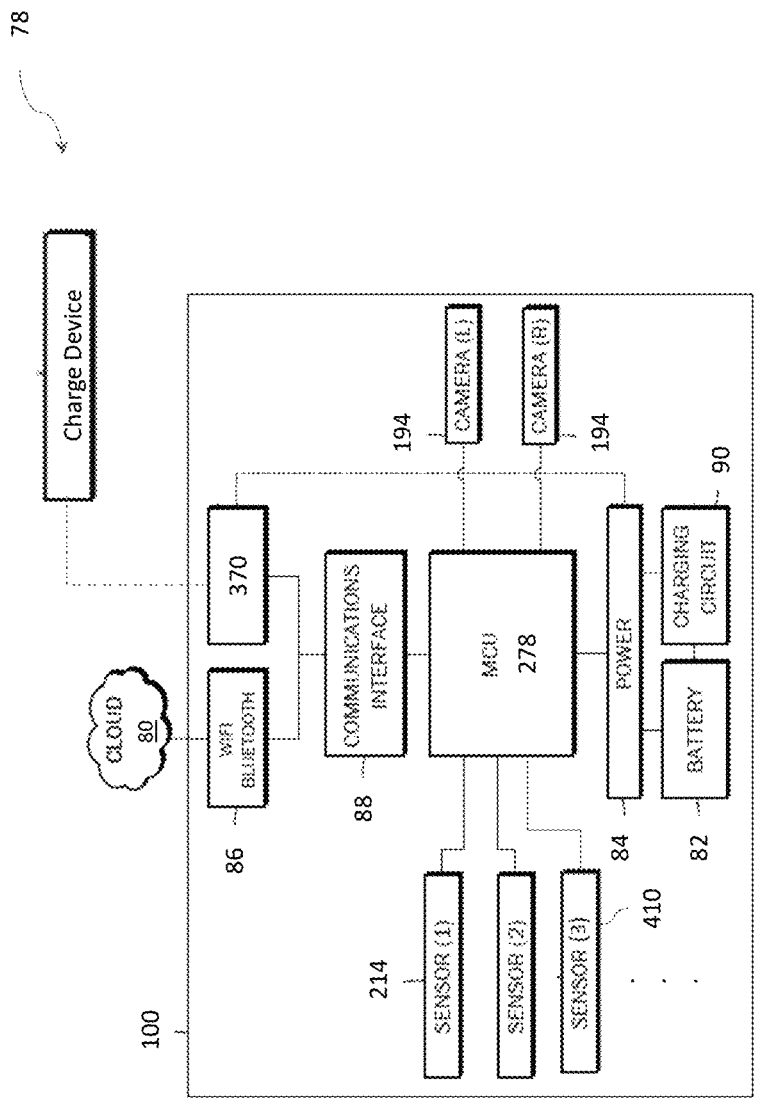
FIG. 1A is a block diagram of the components of the ophthalmic monitoring system.

FIG. 1A shows additional components of the smart spectacles assembly 100 in block format that will be discussed below. For example, the smart spectacles assembly 100 includes one or a plurality of cameras 194 that can capture images of the eye. These images can be processed by the processor 278 of the MCU and stored in a memory of the smart spectacles assembly 100 and/or transmitted to the cloud 80 for processing and/or storage. The smart spectacles assembly 100 also can include a number of other sensors. For example, as discussed further below the smart spectacles assembly 100 can include environmental sensors 214 that can provide additional inputs to the processor 278 for analysis of the condition of the wearer. The sensors can include an inertial measurement unit 410 that can provide a number of functions, as discussed below.

The smart spectacles assembly 100 includes a pair of eyeglasses 104 with lenses that appear much like traditional eyeglasses. The smart spectacles assembly 100 includes a spectacles frame 116 that can include mount points for lenses, hinges and other features. The spectacles frame 116 is formed from a left rim 120A and a right rim 120B. A bridge 122 joins the left rim 120A to the right rim 120B. The spectacles frame 116 holds and supports a right lens 126B. The spectacles frame 116 comprises a front portion of the smart spectacles assembly 100, which is held in front of the wearers eyes such that the left lens 126A and the right lens 126B can provide vision correction if needed or optionally no correction. The spectacles frame 116 can be coupled to stems or temples, e.g., to a left temple 162 and a right temple 166. The left temple 162 and the right temple 166 can be in a wearing position, folded out as shown in FIG. 1 or can be folded into the spectacles frame 116 in a compact manner for storage.

Figure 2:
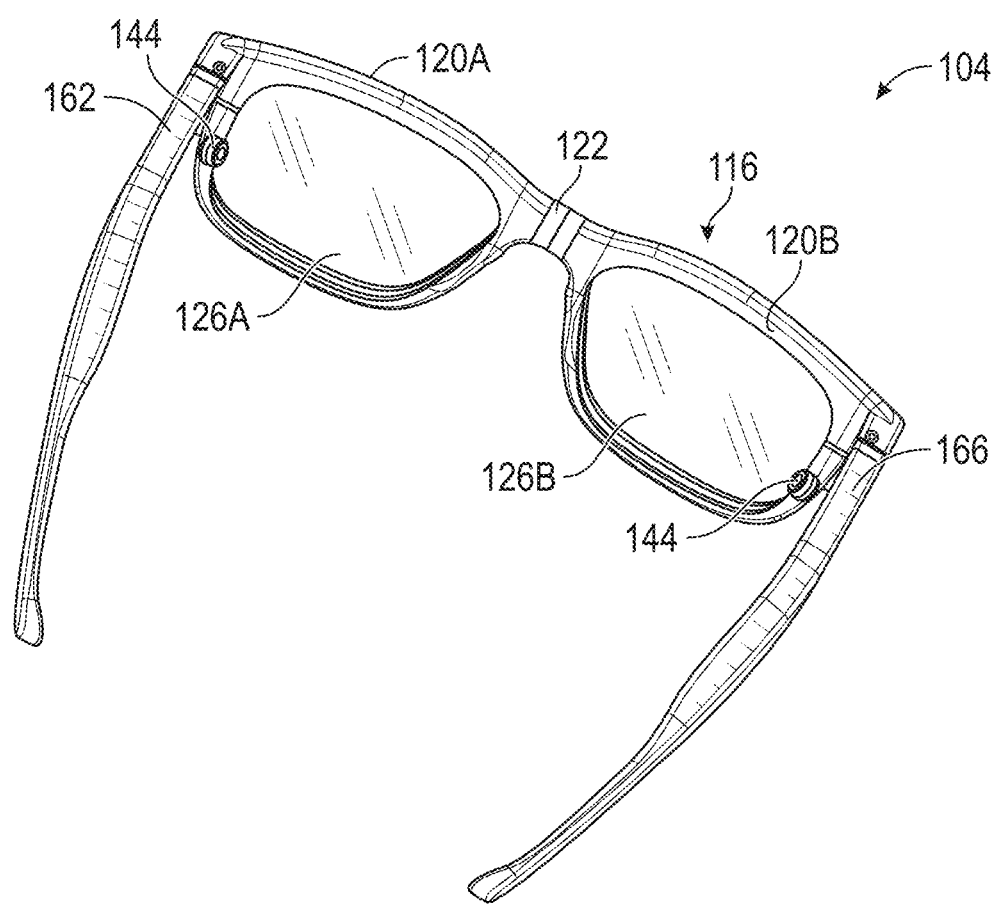
FIG. 2 is a rear perspective view of the spectacles assembly embodiment of FIG. 1.
Figure 2A:
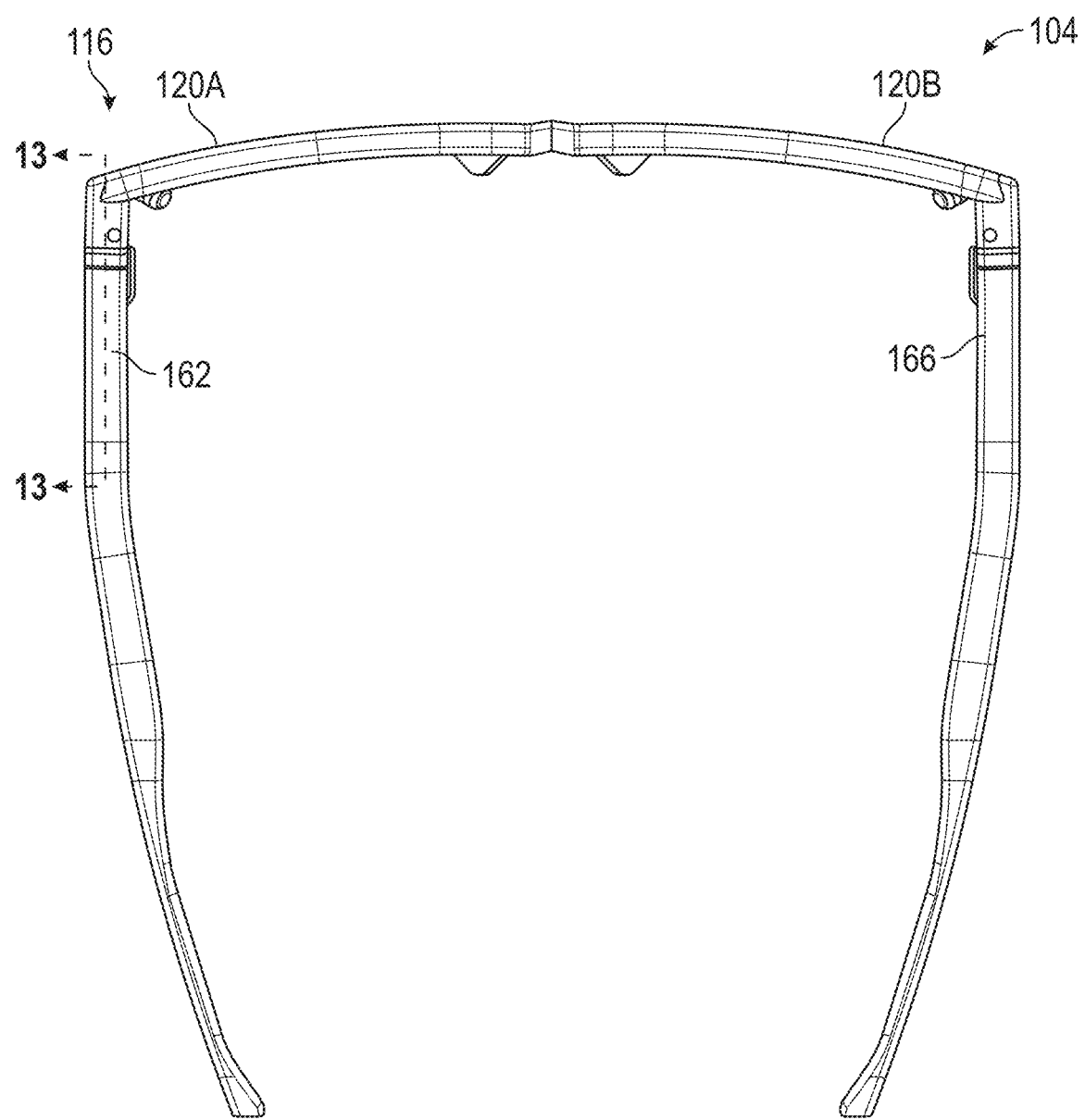
FIGS. 2A and 2B are top and bottom views of the spectacles assembly embodiment of FIG. 1.
Figure 2B:
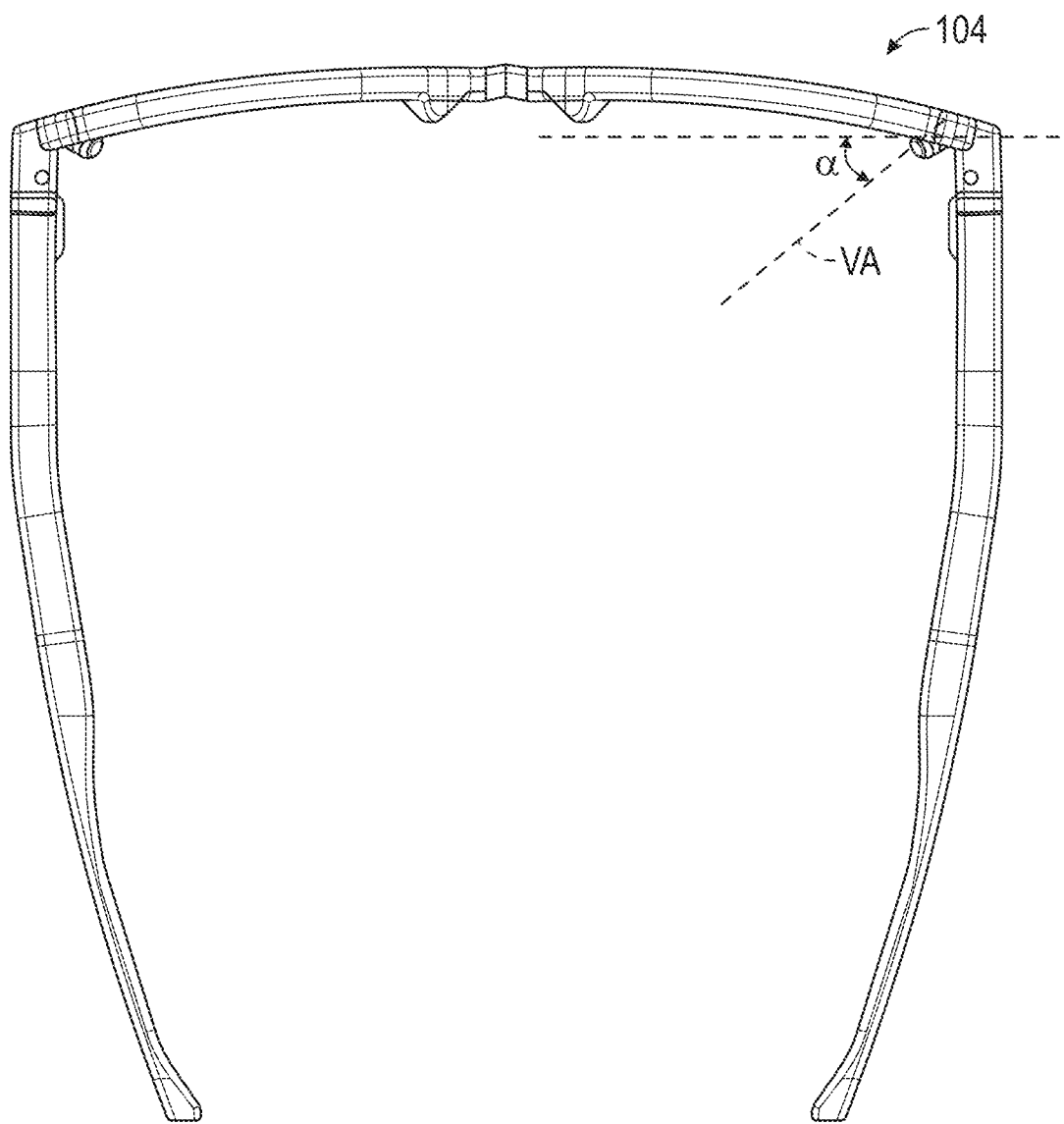
Figure 2C:
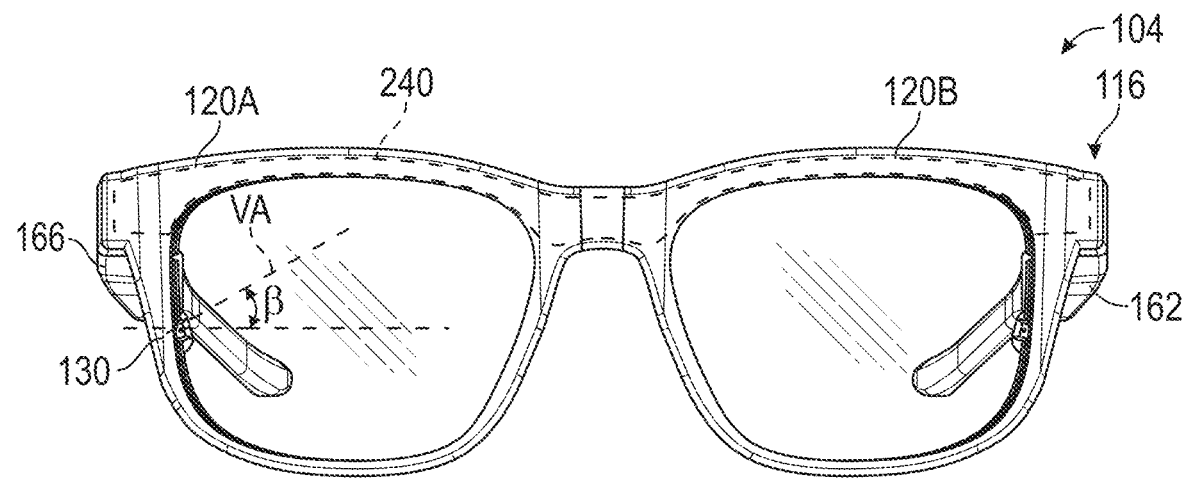
FIGS. 2C and 2D are front and rear views of the spectacles assembly embodiment of FIG. 1.
Figure 2D:
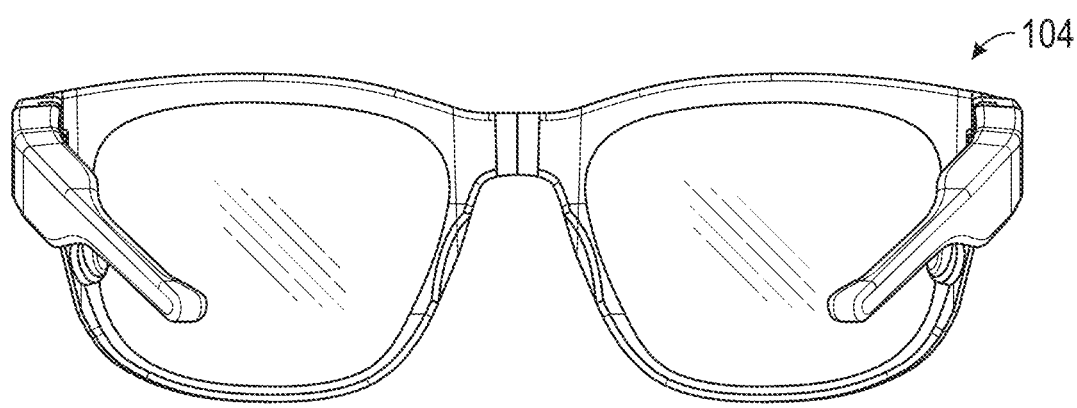
Figure 2E:
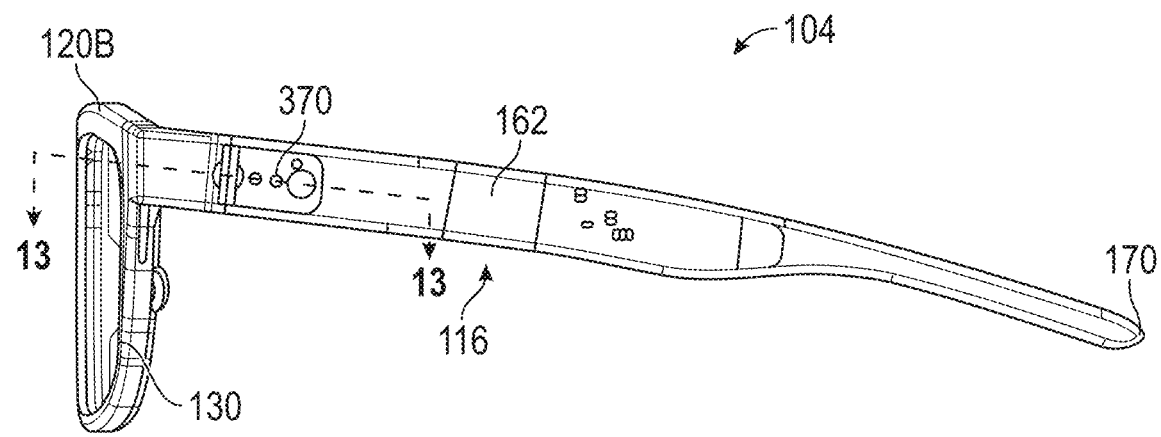
FIGS. 2E and 2F are front and rear views of the spectacles assembly embodiment of FIG. 1.
Figure 2F:
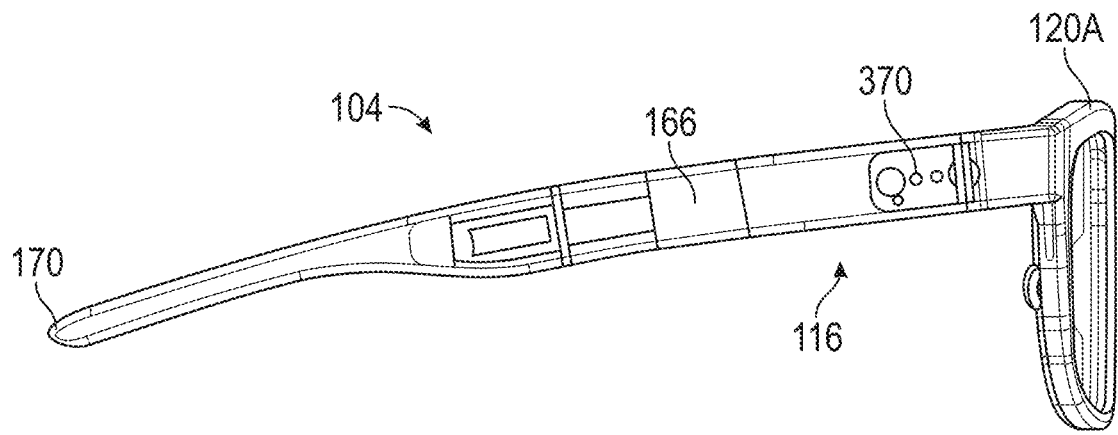

FIGS. 2-2F show the smart spectacles assembly 100 from additional perspectives, illustrating various aspects of the design and utility features of the smart spectacles assembly 100. FIG. 2 shows that eye-facing data acquisition components, such as cameras, imaging device, illuminating devices, environmental sensor and other components can be disposed on each of the left rim 120A and the right rim 120B. The smart spectacles assembly 100 are thus enabled to monitor both eyes to the same extent. In some applications, the smart spectacles assembly 100 can be equipped as shown but configured through software to gather different data and images on the left and right sides. FIGS. 2B and 2C show details of how a camera is mounted to a temporal span 130 of the smart spectacles assembly 100, as discussed further below.

Figure 3:
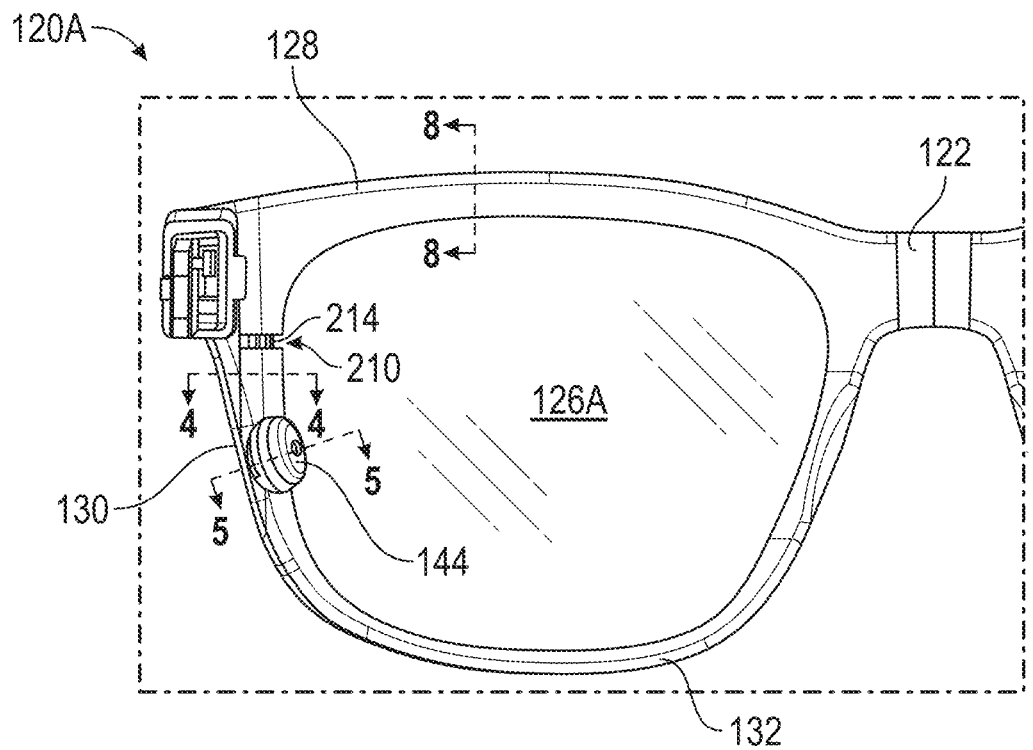
FIG. 3 is a detail view of a camera enclosure disposed on a temporal span of a spectacles frame.

FIG. 3 shows details of additional components of the smart spectacles assembly 100. The left rim 120A can include a superior transverse span 128, the temporal span 130, and an inferior transverse span 132. The superior transverse span 128 can extend from a first end connected to the bridge 122 to an upper portion of the temporal span 130. The inferior transverse span 132 can extend from a lower portion of the temporal span 130 to the bridge 122. The superior transverse span 128, temporal span 130, and inferior transverse span 132 can form a complete, enclosed frame around the left lens 126A. The left rim 120A can have a continuous curvature such that there is not a hard boundary between these sections, e.g., between the temporal span 130 and the inferior transverse span 132. In some embodiments a portion of the left rim 120A is omitted. For example, the inferior transverse span 132 could be replaced by a wire or other tension member to provide a frameless bottom portion. The structure of the right rim 120B can be the same as the structure of the left rim 120A.

The smart spectacles assembly 100 includes an image sensor or camera enclosure 144 disposed on the spectacles frame 116. The camera enclosure 144 can be supported or positioned in any of a number of different locations to provide an ophthalmic observational capability for the smart spectacles assembly 100. In one embodiment, the left rim 120A is configured to support the camera enclosure 144. The left rim 120A can have an anterior segment 134 having an anterior lens mounting edge 136 and a posterior segment 138 having a posterior lens mounting edge 140. The anterior lens mounting edge 136 and the posterior lens mounting edge 140 preferably are planar surfaces that are angled toward each other to provide a V-shaped groove into which an edge of the left lens 126A can be seated as seen toward the left side of FIG. 4. To enhance the compactness of the smart spectacles assembly 100, the camera enclosure 144 preferably is formed into the posterior segment 138. To further enhance the compactness of the smart spectacles assembly 100, the camera enclosure 144 can be formed at least partially at the posterior lens mounting edge 140, e.g., in a break in the posterior lens mounting edge. To further enhance the compactness of the smart spectacles assembly 100, the camera enclosure 144 can be at least partially formed into the anterior lens mounting edge 136. The camera enclosure 144 can extend into a break in the anterior lens mounting edge 136. In the vicinity of the camera enclosure 144, the anterior lens mounting edge 136 and the posterior lens mounting edge 140 may not meet but may be spaced apart by a gap G that provides access to a space configured for routing conductors electrically connecting components of the smart spectacles assembly 100.

Figure 4:
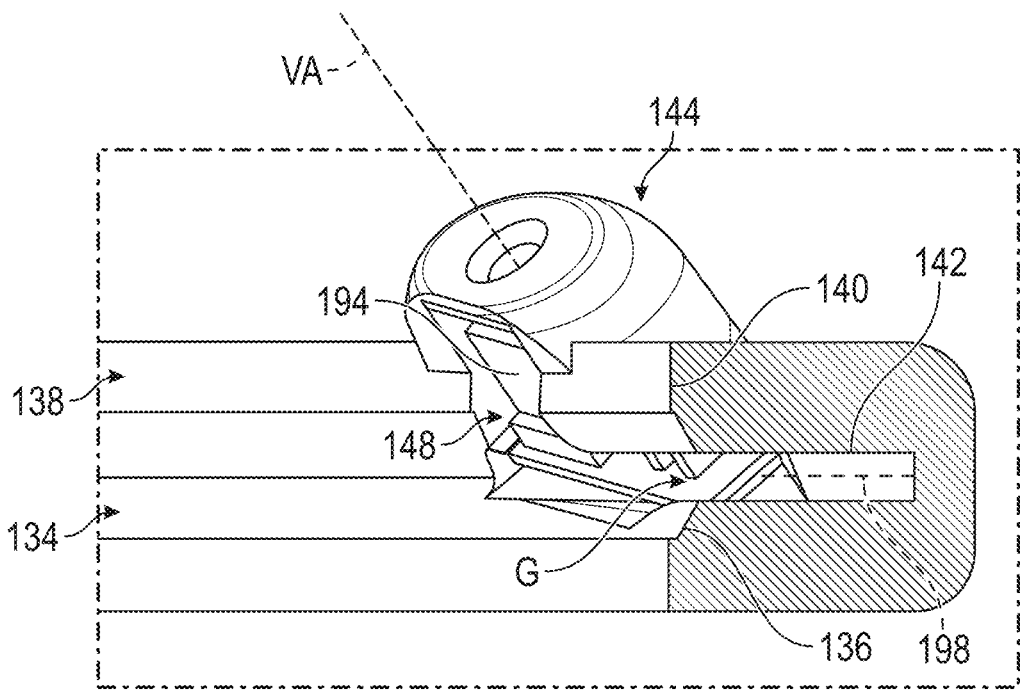
FIG. 4 is a cross-sectional view taken through a flex circuit routing area of the temporal span of the spectacles frame.
Figure 5:
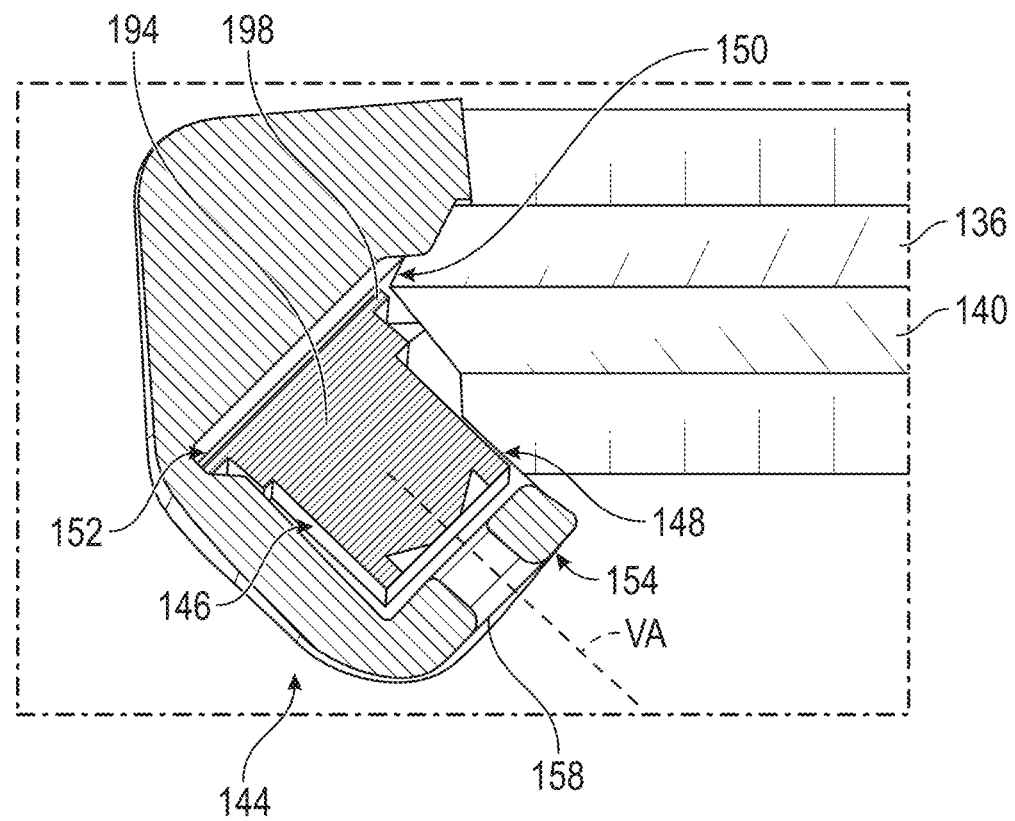
FIG. 5 is a cross-sectional view taken through a camera enclosure disposed on the temporal span of the spectacles frame.

FIG. 5 shows the camera enclosure 144 in greater detail. The camera enclosure 144 cylindrical body extending away from the posterior segment 138. The body can be disposed around, e.g., can surround at least a lateral side of a space 146. The space 146 can extend from a first end 150 disposed at or in a break in the posterior lens mounting edge 140. The space 146 can be disposed interior to the spectacles frame 116. The first end 150 of the space 146 can also extend into the anterior lens mounting edge 136 as seen in FIGS. 4-5. As noted above, by embedding a greater portion of the space 146 within the anterior-to-posterior thickness of the spectacles frame 116 the overall thickness of the smart spectacles assembly 100 is reduced making the smart spectacles assembly more unobtrusive. The space 146 also extends to a second end 154 disposed at or in the camera enclosure 144. The second end 154 is disposed closer to the location of the eye of the wearer when the smart spectacles assembly 100 is being worn. The camera enclosure 144 has an observation aperture 158 locate at or adjacent to the second end 154 of the space 146. The observation aperture 158 preferably is an unobstructed opening. The aperture 158 can be covered in some embodiments to keep an optical surface of an image sensor or camera 194 disposed in the camera enclosure 144 free of debris. FIG. 5 shows that the camera 194 can be recessed within the camera enclosure 144 such that an optical surface of the camera 194 is fully within the space 146, positioned away from the observation aperture 158.

The camera enclosure 144 also has a mounting undercut 152 that helps with fixing the position of the camera 194 within the space 146. The mounting undercut 152 can be located at or adjacent to the first end 150 of the space 146. FIG. 5 shows that the mounting undercut 152 can be a lateral extension of the space 146 into which a conductor 198 can be received. The lateral extension can extend into a lateral wall of the camera enclosure 144. In one embodiment, the conductor 198 can have a rigid edge that can be advanced into the mounting undercut 152 to hold the position of the camera 194 along an axis from the first end 150 to the second end 154 of the space 146. The rigid edge of the conductor 198 can comprise a span of a flex circuit or flex circuit assembly or can include a circuit board to which the camera 194 is mounted.

In one embodiment the camera enclosure 144 can have a C-shaped cross-section with an open side facing toward a lens mounting area of the left rim 120A, as shown in FIG. 5. The same structure can be provided on the right rim 120B. The camera enclosure 144 has an opening 148 on a medial side of the housing. The opening 148 can enable the camera 194 to be moved into the space 146 prior to placing the left lens 126A across the opening 148. This facilitates assembling the camera 194 into the space 146 by simply sliding the camera 194 and the conductor 198 into the space 146 laterally toward the enclosed side of the camera enclosure 144. A circuit board or other rigid extension coupled with the conductor 198 can slide into the mounting undercut 152. Placing the left lens 126A against the anterior lens mounting edge 136 and the posterior lens mounting edge 140 can enclose the camera 194 in the space 146 at least to prevent the camera from coming out of the camera enclosure 144 and preferably to eliminate movement of the camera relative to the observation aperture 158.

As discussed above, the space 146 extends into the thickness of the spectacles frame 116. This provide a lower profile configuration for the smart spectacles assembly 100 overall. The space 146 can extend into the thickness of the left rim 120A by an amount sufficient to allow at least a substantial portion of a body of the camera 194 to be disposed anterior of a posterior side of the posterior segment 138. In various embodiments, about 30 percent, about 35 percent, about 40 percent, about 45 percent, about 50 percent, about 55 percent, about 60 percent, about 65 percent, about 70 percent, about 75 percent, about 80 percent, about 90 percent, about 100 percent, or any range of including two of the foregoing numbers as end points of the height of the camera 194 can be disposed within the thickness of the left rim 120A, e.g., between the posterior surface of the posterior segment 138 and an anterior surface of the anterior segment 134. If the camera 194 is entirely disposed within the thickness of the left rim 120A, the camera enclosure 144 may be provided entirely within a portion of the temporal span 130 of the rim. The observation aperture 158 can be disposed on the posterior surface of the posterior segment 138 of the left rim 120A or can be disposed on a projection such that a viewing angle is oriented as appropriate, e.g., as discussed below.

Figure 5A:
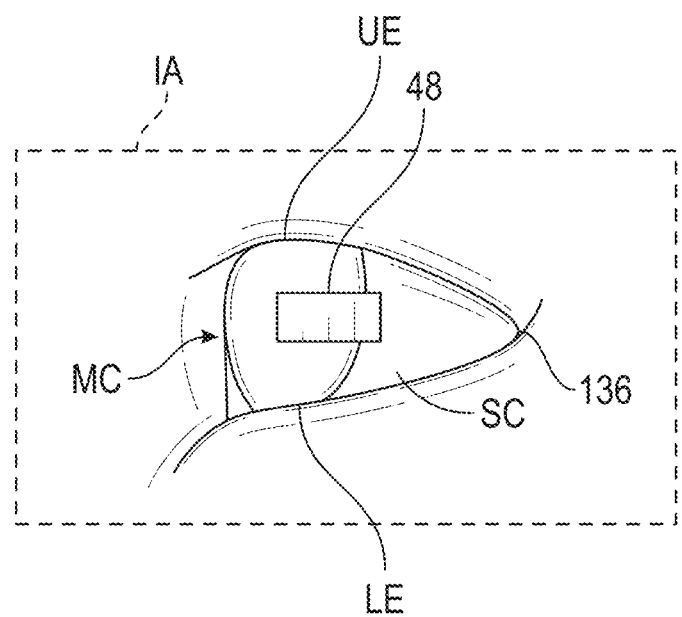
FIG. 5A is a side-view of an eye depicting an imaging area of the eye.

The camera 194 is configured to capture images of a portion of an eye or an area around the eye of the wearer of the smart spectacles assembly 100. In one approach, the camera 194 is oriented toward a lateral side of the eye of the wearer. FIG. 5A shows that the camera 194 can be configured and mounted in the camera enclosure 144 to capture images of a portion of the eye and surrounding tissue in an imaging area IA. The camera 194 can capture an image including a lateral canthus LC of the eye to a medial portion of a cornea MC of the eye and from a lower eyelid LE of the eye to an upper portion the cornea and/or an area above an upper eyelid UE when the eye is aligned with an anterior-posterior direction. In some approaches, the imaging area includes at least a portion of the sclera SC of the eye. Thus, the camera 194 can capture an imaging area of interest of the eye including anatomy that may be indicative of an ophthalmic condition. The imaging area IA can extend to skin surfaces on all sides of the eye under observation such that the image can include the entire eye visible from the vantage of the camera 194. The camera 194 can capture non-anatomical objects, structures, or features in the imaging area IA as well. In one example, a wearer is being treated for an eye condition by a patching protocol. The patient may be suffering from amblyopia and may have been instructed by a healthcare professional to wear a patch at least a minimum amount of time per day. The camera 194 can detect the presence of an eye patch and can track the amount of time that the eye patch is worn. This information can be stored in memory on the smart spectacles assembly 100 and can be transferred to the cloud 80 and to the healthcare professional to monitor compliance with the patching protocol. FIG. 5A shows another example of non-anatomical structure image capture in which the camera 194 captures reflections on the eye, e.g., a reflection 48 of an image of a screen that the eye may be directed toward. The smart spectacles assembly 100 can track the amount of time that a wearer spends focused on screens as a metric of ophthalmic health. In one example, the smart spectacles assembly 100 can detect how close or far the screen causing the reflection 48 is from the wearer based on the size of the reflection 48. For example, the rectangular reflection 48 could be captured by the camera 194 and the smart spectacles assembly 100 can calculate a distance from the eye to the screen that is reflected. The smart spectacles assembly 100 also can monitor the duration of time that the wearer is focused on the screen that generates the reflection 48. For patients predisposed to or suffering from myopia, too much time focusing on close objects (e.g., a screen seen in the reflection 48) can worsen the condition. Thus, the smart spectacles assembly 100 can be a powerful tool for detecting and tracking both anatomical and non-anatomical image-based conditions or events relevant to a variety of ophthalmic treatments and conditions.

In some embodiments the camera enclosure 144 is oriented such that a viewing axis VA of the camera 194 is disposed through the observation aperture 158 in a direction to intersect the imaging area IA when the smart spectacles assembly 100 is worn. The camera enclosure 144 can be oriented such that the viewing axis VA of the camera 194 is disposed through the observation aperture 158 in a medial direction. The camera enclosure 144 can be oriented such that the viewing axis VA of the camera 194 is disposed through the observation aperture 158 in an upwardly direction. Various viewing angles VA can be provided. FIG. 2B shows that the viewing axis VA can be measured medially or as an angle α inclined relative to a vertical plane. The angle α can be about 15 degrees, about 20 degrees, about 25 degrees, about 30 degrees, about 35 degrees, about 40 degrees, about 45 degrees, about 50 degrees, about 55 degrees or any range of degrees extending between any of the foregoing values as endpoints. The viewing axis VA of the camera 194 can be disposed perpendicular to the first end 150 of the space 146, e.g., to the observation aperture 158. FIG. 2C shows that the viewing axis VA can be oriented upwardly at an angle β relative to a horizontal plane. The angle β can be about 5 degrees, about 10 degrees, about 15 degrees, about 20 degrees, about 25 degrees, about 30 degrees, about 35 degrees, about 40 degrees, about 45 degrees, about 50 degrees, about 55 degrees or any range of degrees extending between any of the foregoing values as endpoints. In one example embodiment, the angle α is about 33.3 degrees and the angle β is about 14.5 degrees. In another example embodiment, the angle α is about 34.2 degrees and the angle β is about 21.7 degrees.

The foregoing description has focused on the camera enclosure 144 and the camera 194 as being disposed on the temporal span 130 on the left rim 120A of the smart spectacles assembly 100. The smart spectacles assembly 100 can include a second camera enclosure and a second camera disposed on a temporal span 130 of the right rim 120B, as seen in FIG. 2. Providing a camera on each of the left rim 120A and the right rim 120B allows independent monitoring of each of the left eye and the right eye. By providing two cameras, the same or different monitoring functionalities are made possible by the smart spectacles assembly 100. The left or the right eye of the wearer of the smart spectacles assembly 100 can be monitored more or less extensively in various techniques. Different ophthalmic or other health conditions can be monitored through left and right cameras 194.

The camera 194 in the smart spectacles assembly 100 provides the capability to capture high resolution imaging when the circumstances require or permit. The smart spectacles assembly 100 can provide other sensing capabilities for the same or for different situations. The smart spectacles assembly 100 can include one or more sensor windows 210 (e.g., an environmental sensor windows) for sensing or controlling aspects of the performance of the smart spectacles assembly 100 or of the eye of the wearer. FIG. 3 shows that in one embodiment, a sensor window 210 is provided on the spectacles frame 116, e.g., on the left rim 120A of the frame. The sensor window 210 can be disposed on the posterior segment 138 of the left rim 120A.

In one embodiment, the sensor window 210 is provided to provide a detection path for a sensor configured to detect an ocular parameter. The sensor window 210 can be disposed on the temporal span 130. The sensor window 210 can be disposed above the camera enclosure 144. The sensor window 210 can include a slot or recess formed in the left rim 120A. The slot or recess are examples of an opening that can allow a sensor 214 to detect a signal from the eye of the wearer. The sensor 214 can detect a reflection of the eye of the wearer. The reflection detected by the sensor 214 can include a reflection of ambient light. The sensor 214 can detect a reflection of a light source disposed outside of the smart spectacles assembly 100, e.g., a reflection of a screen 48 or otherwise reflected light. The sensor 214 can include a light sensor. The reflection detected by the sensor 214 can include a reflection of light emitted by the smart spectacles assembly 100. In one embodiment, the sensor 214 can be configured to both emit light and detect light reflected from the eye of the wearer.

The sensor window 210 can enable a sensor disposed therein to detect a patient parameter that may not be limited to an ophthalmic parameter. For example, a temperature sensor could be positioned at, in or adjacent to the sensor window 210. The temperature sensor can be directed toward the patient to detect heat from the wearer. The temperature sensor can detect when the smart spectacles assembly 100 are being worn by distinguishing a heat level while being worn (generally higher) from an ambient temperature (generally lower) when the smart spectacles assembly is not being worn. The smart spectacles assembly 100 can be configured to detect changes in stead-state temperature consistent with removing the smart spectacles assembly from changes consistent with departing a warm environment to enter a cold environment while still wearing the glasses. The ambient sensor is one example of an environmental sensor that can be provided in the smart spectacles assembly 100, e.g., positioned to detect an environmental condition in and around the smart spectacles assembly. Another example is a humidity sensor. A humidity sensor can provide a basis for evaluating whether an eye under observation is suffering from dry eye conditions and/or is merely subject to a dry environment, or both.

The sensor window 210 and the sensor 214 can enable a low power mode for certain actions. For example, a low power infrared ("IR") sensor 214 utilizing infrared light could be provided to detect blinks. While blink detection could be provided by capturing high resolution images, a non-image optical signal could also be analyzed to detect blinks using a single pixel light sensitive (e.g., infrared-sensitive) light detector.

Figure 6:
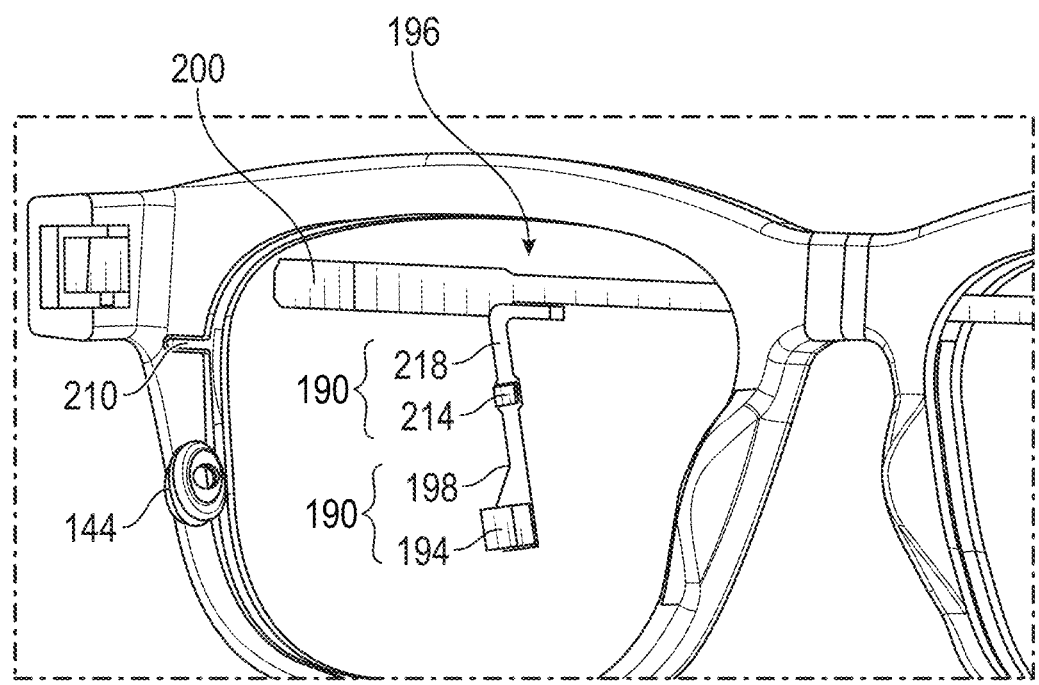
FIG. 6 is a rear view of a smart spectacles frame assembly including a spectacles frame and a flex circuit assembly, illustrating a step of assembly of the smart spectacles frame assembly.

Although the camera 194 and the sensor 214 (where included) could be wired in any suitable manner, FIG. 6 shows that in one embodiment a flex circuit 196 is provided for electrically connecting other components to a camera assembly 190 including the camera 194 and a conductor 198. The conductor 198 can be embedded in a portion of a flex circuit 196 configured to connect the camera 194 with a processor 278 and/or a battery 394, as discussed further below. The conductor 198 can conduct power to the camera 194 from the battery 394. The conductor 198 can conduct image signals or sensor signals from the camera 194 to the processor 278 disposed on a circuit board 274 disposed in the left temple 162 or to a processor in the right temple 166. The flex circuit 196 can have a first span configured to extend to a terminal end 200 configured to be engaged with the circuit board 274 disposed in left temple 162. The first span can also extend to and in some cases through the bridge 122 of the spectacles frame 116. The flex circuit 196 can have a second portion configured to extend from a mid-portion of the first span to the camera 194. The second portion can include the conductor 198 extending from the camera 194. The second portion can include a second conductor 218 extending from the sensor 214. The second conductor 218 can conduct power to the sensor 214. The second conductor 218 can conduct sensor signals from the sensor 214 to the circuit board 274 and/or across the bridge 122 to a processor disposed in the right temple 166. The conductor 218 can conduct sensor signals from the sensor 214 to more than one processor, e.g., to a processor disposed on the right temple 166 and to a processor disposed on the left temple 162. The conductor 218 can conduct power from the right temple 166 or the left temple 162 to the sensor 214.

The routing of the flex circuit 196 is accommodated by one or more channels formed in the spectacles frame 116. FIG. 4 shows that a u-shaped inner periphery 142 can be provided in the temporal span 130 of the left rim 120A. The u-shaped inner periphery 142 can have a posterior facing surface disposed on the anterior segment 134 of the left rim 120A of the spectacles frame 116. The posterior facing surface can extend from the anterior lens mounting edge 136 to a medial facing wall of a lateral portion of the temporal span 130. The u-shaped inner periphery 142 can have an anterior facing surface disposed on the posterior segment 138 of the left rim 120A of the spectacles frame 116. The anterior facing surface can extend from the posterior lens mounting edge 140 to the medial facing wall of the lateral portion of the temporal span 130. A dashed line in FIG. 4 illustrates that the conductor 198 from the camera 194 extends upward in u-shaped inner periphery 142 to the sensor window 210.

Figure 7:
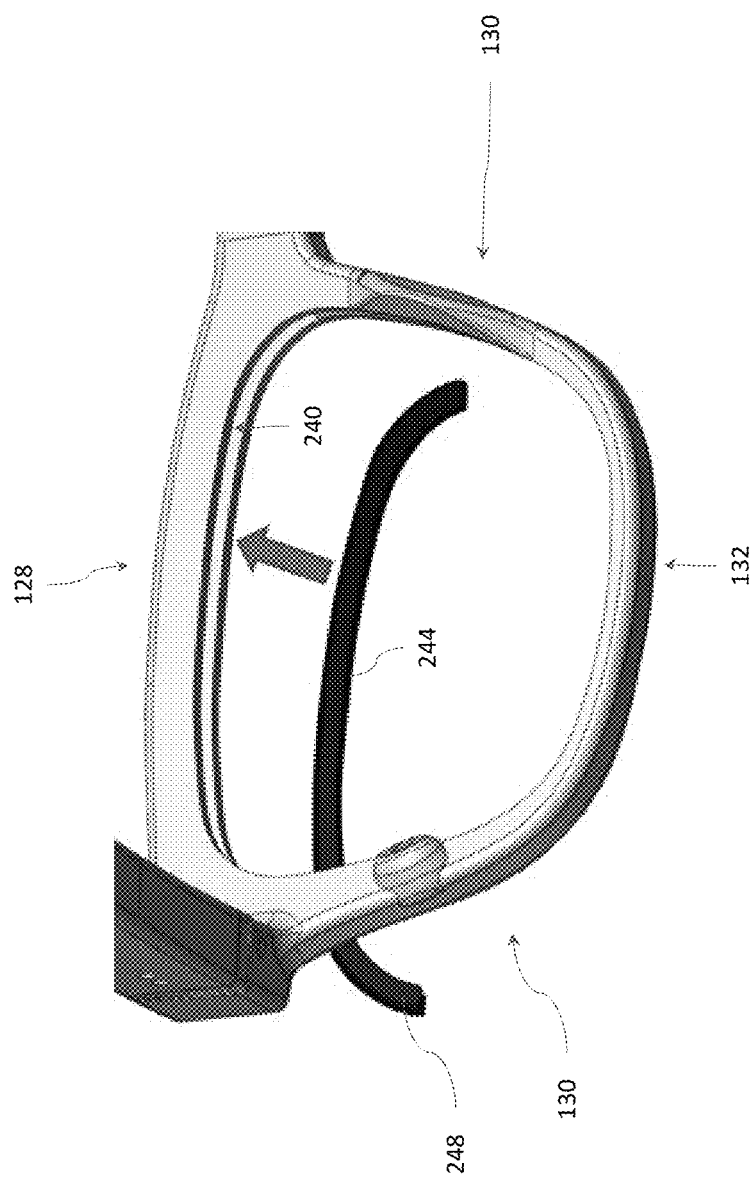
FIG. 7 is a bottom perspective view of the smart spectacles frame assembly of FIG. 6, illustrating a closure for enclosing a conductor passage for routing the flex circuit seen in FIG. 6.

As noted above, the smart spectacles assembly 100 is configured to provide for electrical signals and power through the spectacles frame 116. At the same time, it is desired to maintain the smart spectacles assembly 100 similar in appearance to spectacles only equipped for vision correction. FIGS. 2C, 6-7 show additional structures for integrating the flex circuit 196 into the spectacles frame 116. The u-shaped inner periphery 142 comprises an example of a conductor passage in the spectacles frame 116 for the conductor 198 and the second conductor 218. The spectacles frame 116 also can be provided with one or more conductor passages 240 (see, e.g., FIGS. 2C and 7) for receiving the transverse span of the flex circuit 196. The conductor passage 240 is configured to house the transverse span, e.g., the span of the flex circuit 196 that extends from the second conductor 218 toward the opposite side of the smart spectacles assembly 100. The conductor passage 240 also can house a portion of the flex circuit 196 extending from the second conductor 218 to the terminal end 200.

In one embodiment, the conductor passage 240 is formed in the spectacles frame 116. The conductor passage 240 can comprise a blind recess formed in the superior transverse span 128 into which the flex circuit 196 can be disposed. The conductor passage 240 can include portions disposed in the superior transverse span 128 of each of the left rim 120A and the right rim 120B. The conductor passage 240 can extend continuously from adjacent to the left temple 162, through the bridge 122, to adjacent to the right temple 166. While the superior transverse span 128 on the left rim 120A and the superior transverse span 128 on the right rim 120B can be an advantageous location for the flex circuit 196, it is desired that the flex circuit 196 be hidden and protected within the smart spectacles assembly 100. A closure 248 can be provided to retain the flex circuit 196, while keeping the flex circuit out of sight and protected within the smart spectacles assembly 100. The closure 248 can serve to seal the conductor passage 240 to keep moisture from contacting components disposed therein. The closure 248 can be press-fit into conductor passage 240 to close the passage.

Figure 8A:
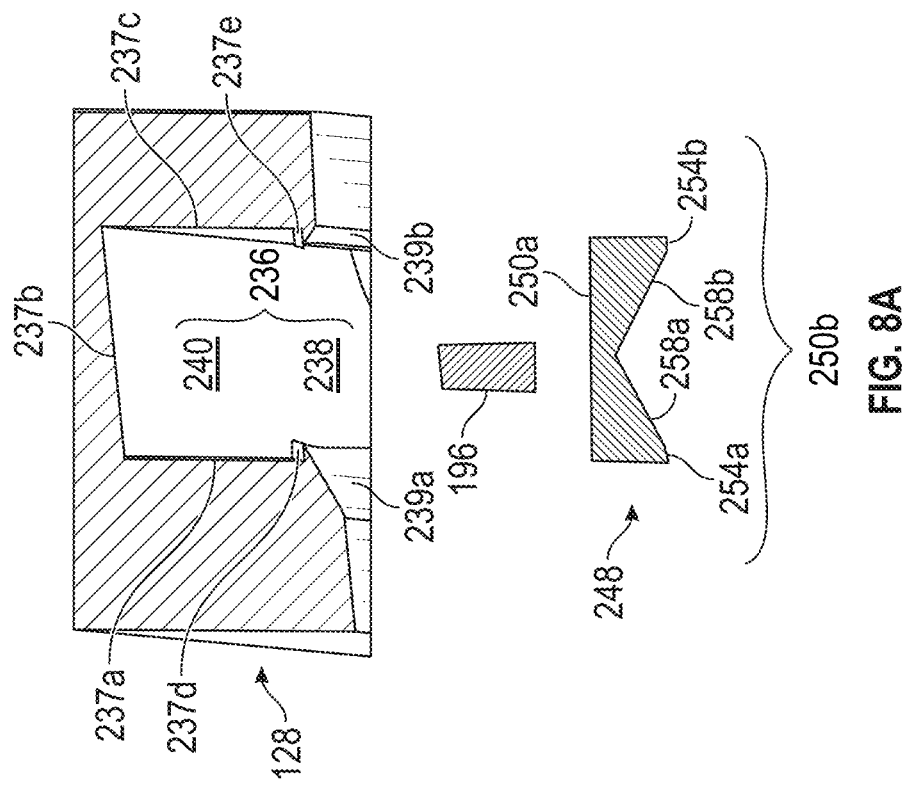
FIG. 8A is an exploded view of the flex circuit, the superior transverse span, and the closure according to one embodiment.
Figure 8:
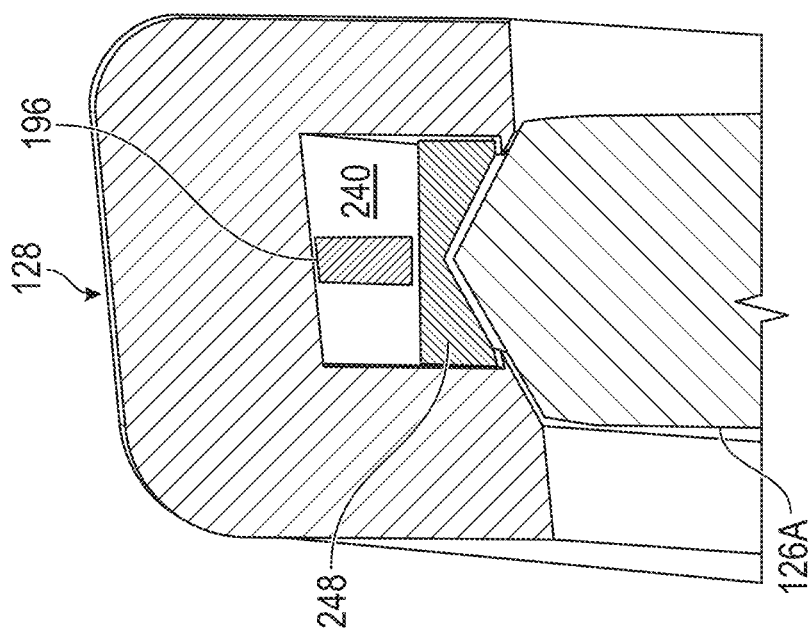
FIG. 8 is a cross-sectional view of the smart spectacles frame assembly taken through the superior transverse span of the spectacles frame at the section plane 8-8 seen in FIG. 3.

FIGS. 7, 8, and 8A illustrate approaches to integrating the flex circuit 196 into the conductor passage 240. The conductor passage 240 can be a portion of a blind recess 236 formed in the superior transverse span 128. The conductor passage 240 can include the deepest portion of the blind recess 236. A shallower portion of the blind recess 236 can include a lens edge zone 238. The lens edge zone 238 of the blind recess 236 of the superior transverse span 128 of the left rim 120A can be configured to engage a portion of the left lens 126A (e.g., having or configured to have a spectacles frame engagement portion). The lens edge zone 238 can include a lens mounting edge 239a on a posterior side thereof and a lens mounting edge 239b on an anterior side thereof. FIG. 8 shows that the lens mounting edge 239a can engage a posterior angled portion of a periphery of the left lens 126A. FIG. 8 shows that the lens mounting edge 239b can engage an anterior angled portion of a periphery of the left lens 126A. The blind recess 236 can include a posterior wall 237a, a downward facing wall 237b, and an anterior wall 237c. The walls 237a, 237b, 237c define a space sized to receive and retain the flex circuit 196. The blind recess 236 also can include at least one of a posterior inferior ledge 237d and an anterior inferior ledge 237e configured to engage the closure 248.

The closure 248 can include a superior or upper side 250a and an inferior or lower side 250b. The inferior side 250b can include a posterior retention portion 254a and an anterior retention portion 254b. The inferior side 250b can include a posterior lens portion 258a and an anterior lens portion 258b and a central portion located between the posterior lens portion 258a and the anterior lens portion 258b. The central portion can be a junction of or between the posterior lens portion 258a and the anterior lens portion 258b. The posterior lens portion 258a can be formed to provide a continuation of the angled surface of the lens mounting edge 239a when the closure 248 is disposed in the blind recess 236. The anterior lens portion 258b can be formed to provide a continuation of the angled surface of the lens mounting edge 239b when the closure 248 is disposed in the blind recess 236. When the closure 248 is advanced through the lens edge zone 238 of the blind recess 236, angled surfaces from the lens mounting edge 239a to the posterior lens portion 258a of the inferior side 250b can engage one of the peripheral angled edges of the left lens 126A. The inferior side can have a lens mounting recess 244. The posterior retention portion 254a and the anterior retention portion 254b can have any suitable shape, e.g., disposed along the same angle as the posterior lens portion 258a and the anterior lens portion 258b. The posterior retention portion 254a and the anterior retention portion 254b can at an angle to the posterior lens portion 258a and the anterior lens portion 258b, e.g., at a higher angle to a vertical direction up to and including transverse to a vertical direction. The posterior retention portion 254a and the anterior retention portion 254b can be flat or rounded. When the closure 248 is advanced through the lens edge zone 238 of the blind recess 236, angled surfaces from the lens mounting edge 239b to the anterior lens portion 258b of the inferior side 250b can engage the other of the peripheral angled edges of the left lens 126A.

The closure 248 can be secured in the blind recess 236 in any of a number of ways. The closure 248 can be configured to be supported from below by an underhung portion of the superior transverse span 128 of the left rim 120A. For example, in one embodiment the posterior inferior ledge 237d can extend under the posterior retention portion 254a of the closure 248 to retain the closure within the blind recess 236. In one embodiment an anterior inferior ledge 237e can extend under the anterior retention portion 254b of the closure 248 to retain the closure within the blind recess 236. In one embodiment, the closure 248 is supported in an anterior portion and in a posterior portion, e.g., by the anterior inferior ledge 237e and by the posterior inferior ledge 237d respectively. The ledges or other under hangs where provided constrict the side of the blind recess 236 at the lens edge zone 238. The conductor passage 240 can have a widened anterior-posterior dimension above the lens edge zone 238. The anterior-posterior dimension of the closure 248, which may be referred to as a thickness, can be greater than the narrowed dimension at the lens edge zone 238 but equal to or less than the anterior-posterior dimension of the conductor passage 240 of the lens edge zone 238. In one method of assembly the closure 248 is compressed in its thickness direction or dimension upon entering the lens edge zone 238 to pass through the narrowed region of the blind recess 236. The closure 248 can have a resilient construction such that the superiorly directed compression force deforms (e.g., elastically deforms) the closure 248 during the insertion of the lens, such that afterwards it may return to its uncompressed dimension or state upon reaching the conductor passage 240.

In other embodiments, the closure 248 can be configured such that the thickness in the anterior-posterior direction is the same or greater than the conductor passage 240. The securement of the closure 248 in the blind recess 236 can be achieved at least in part by friction or an expansion pressure of the closure 248 against the inside walls of the blind recess 236. An anterior surface of the closure 248 can expand to apply a pressure to the anterior wall 237c of the blind recess 236. A posterior surface of the closure 248 can expand to apply a pressure to the posterior wall 237a of the blind recess 236, such that the closure 248 is press-fit into the blind recess 236. That is, the closure 248 can be coupled with the recess 236 by press-fitting. The pressures can correspond to a frictional engagement between the closure 248 and the blind recess 236. A pressure or friction between the closure 248 and the blind recess 236 can be combined with an underhung to enhance retention of the closure. In some embodiments, pressure and frictional engagement can be sufficient to allow for retention of the closure 248 without any under hangs. In other embodiments, an adhesive can be used to secure the closure 248 in the blind recess 236. In other embodiments, an adhesive can be used to secure the superior side 250a to a lower surface of the superior transverse span 128 spanning and covering the blind recess 236. An adhesive could be combined with an underhung portion as shown and described in connection with FIGS. 8 and 8A. An adhesive could be combined with a pressure fit between the closure 248 and the walls of the blind recess 236.

Figure 9:
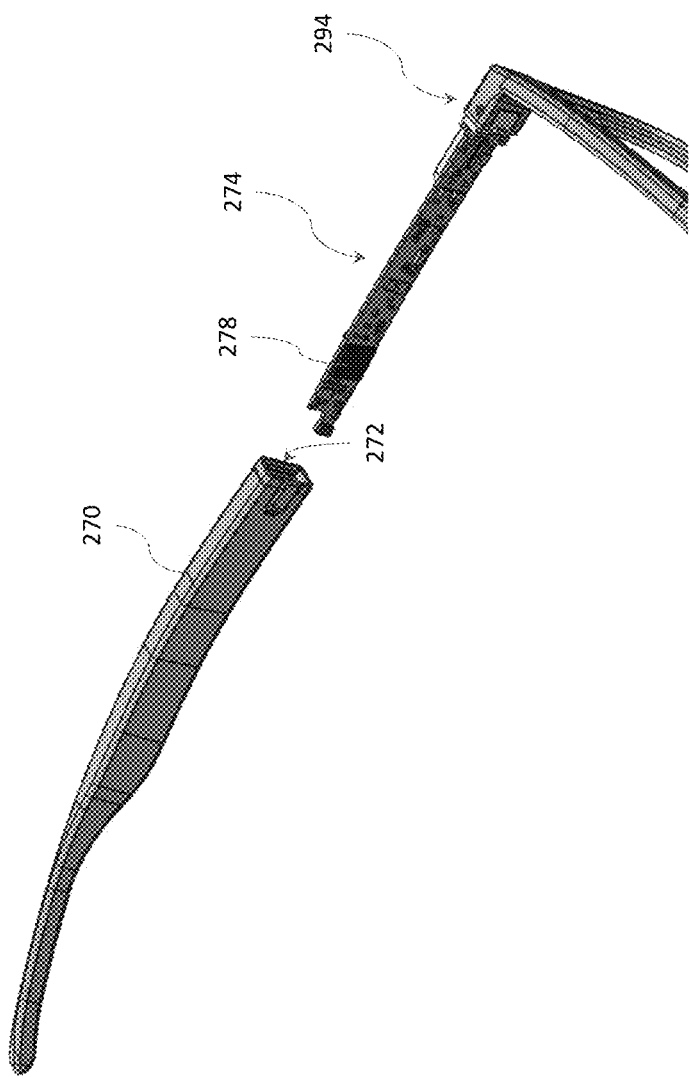
FIG. 9 is an exploded view of a left side of the smart spectacles frame assembly showing the left temple spaced apart from a circuit board configured to be disposed in the left temple.

FIGS. 9-18C show more detail of techniques for routing of the flex circuit 196 through the spectacles frame 116 and for coupling the flex circuit 196 to other electrical components of the smart spectacles assembly 100. FIG. 9 shows the left temple 162 in a partial exploded view. An elongate body 270 forming an exterior surface of the left temple 162 is shown separated from a circuit board 274. The circuit board 274 includes a processor 278 and other components discussed further below. The circuit board 274 can be inserted into a blind recess 272 of the elongate body 270. The blind recess 272 encloses a volume shaped and sized to receive the circuit board 274. The blind recess 272 can extend in the temple toward a temple tip 170. Each of the left and right temple 162, 166 can have a temple tip 170. The circuit board 274 is configured to be coupled with the spectacles frame 116 at a hinge assembly 294 (e.g., including a hinge mount feature). The elongate body 270 can be configured such that when the circuit board 274 is inserted into the recess 272, the elongate body 270 and the spectacles frame 116 have a seamless outer periphery disposed around the recess 272.

Figure 10:
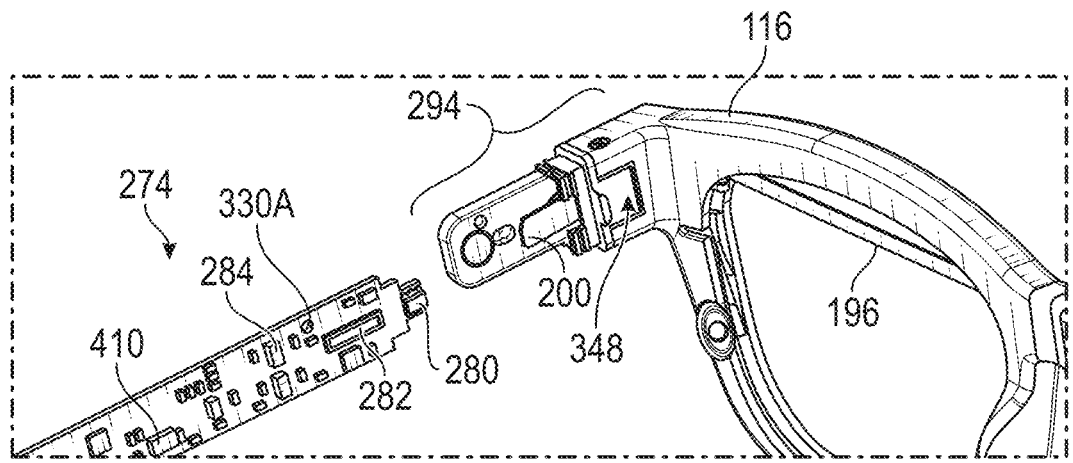
FIG. 10 is an exploded view of a sub-assembly of the left side of the smart spectacles frame assembly, showing the circuit board spaced apart from a hinge assembly configured to couple the left temple to the spectacles frame.
Figure 11:
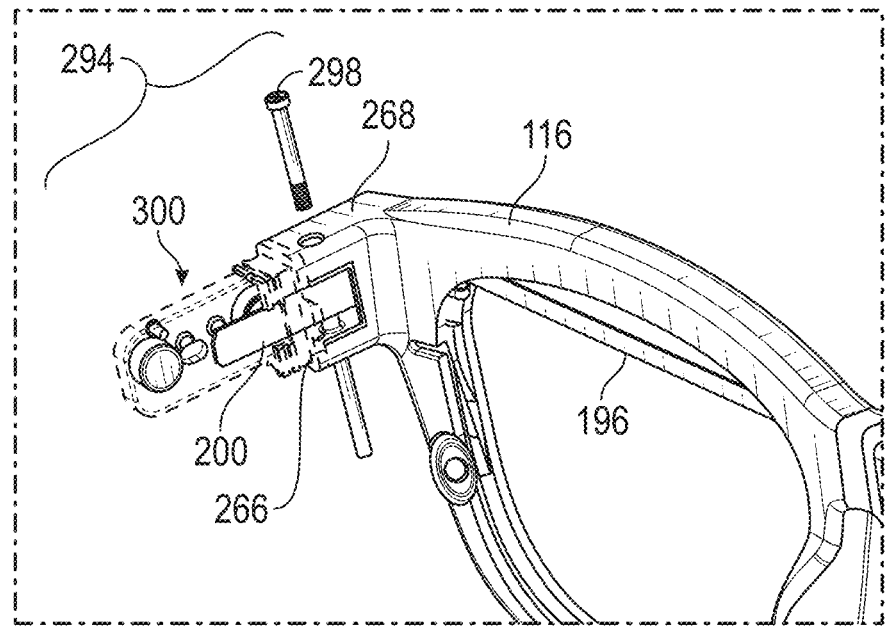
FIG. 11 is an exploded view of a sub-assembly of the left side of the smart spectacles frame assembly, showing components of an axle spaced apart other aspects of the hinge assembly.

FIG. 10 shows the circuit board 274 separated from the hinge assembly 294, revealing the position of the terminal end 200 of the flex circuit 196 which is routed through the hinge assembly 294 as discussed further below. The hinge assembly 294 can have an axle 298 (see FIGS. 11-12) or other pivot configured to mate with a lower mount point 266 and an upper mount point 268. The lower mount point 266 and the upper mount point 268 can be molded projections of the spectacles frame 116. The mount points 266, 268 are seen in FIG. 11. The hinge assembly 294 can include a rotatable member 300 opposite to the axle 298. The rotatable member 300 is rotatable about the axle 298 or other pivot to provide for folding the left temple 162 against the posterior side of the spectacles frame 116 and unfolding the left temple 162 to the position as shown in FIGS. 1-2F.

Figure 12:
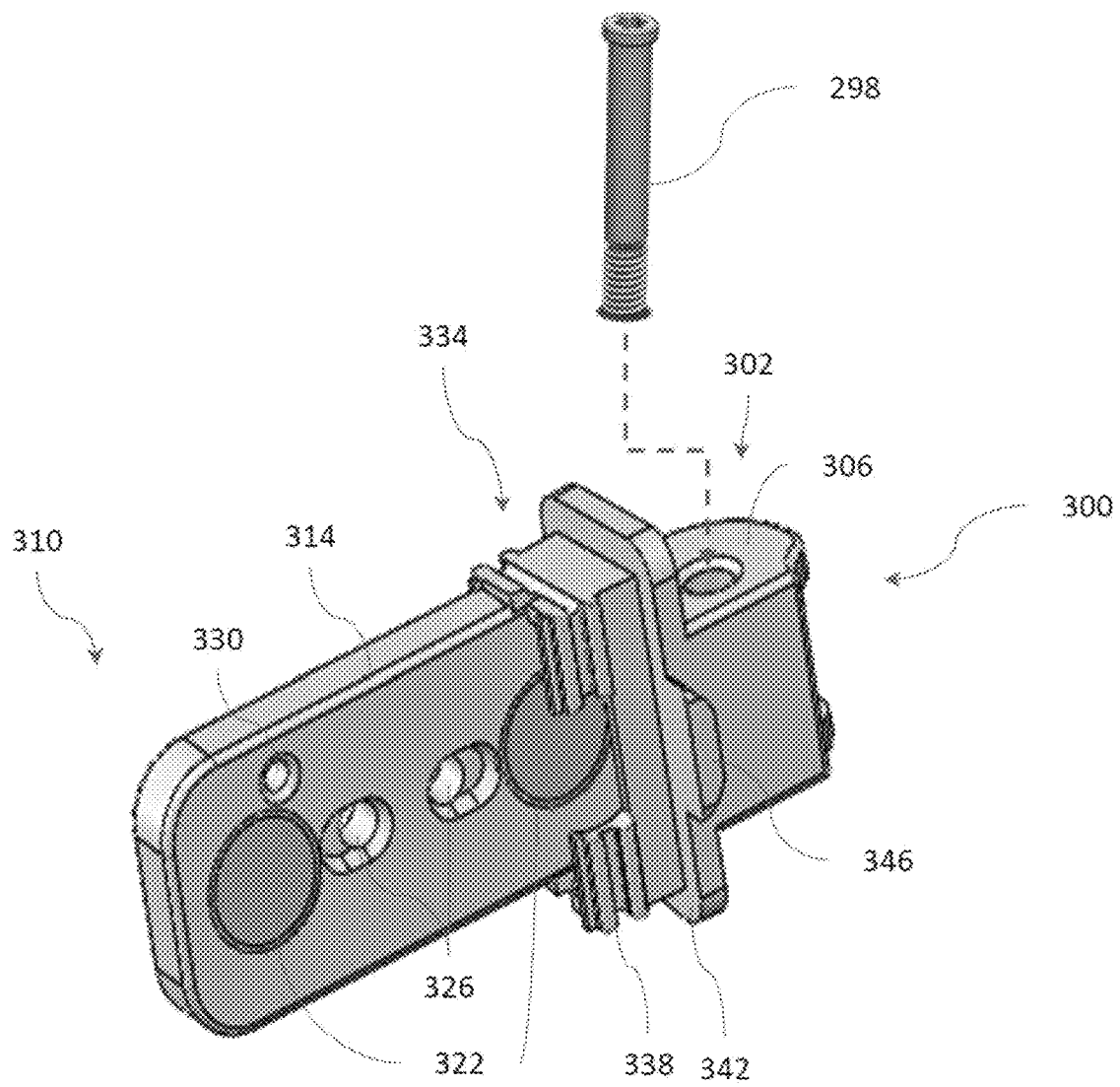
FIG. 12 shows the hinge assembly of FIG. 11 separated from the spectacles frame and the left temple.

FIGS. 11 and 12 show additional details of the hinge assembly 294 and the rotatable member 300. The rotatable member 300 can have a first end 302 and a second end 310 opposite to the first end 302. The first end 302 can include a rotatable body comprising a barrel 306 having a passage disposed therethrough for receiving the axle 298. The barrel 306 can have a rounded surface 306a (see FIG. 13) for rotating relative to the spectacles frame 116. The rotatable member 300 has a flange 314 opposite to the barrel 306. The flange 314 has a plurality of features for housing or mounting other components. An anchor point 330 can be provided for securing a mount point 330A of the circuit board 274 to the flange 314. For example, a screw can be used to secure the circuit board 274 to the flange 314 through the anchor points 330, 330A.

The flange 314 also provides a location along which the terminal end 200 of the flex circuit 196 is connected to the circuit board 274. When the circuit board 274 is secured to the flange 314 by connection through the anchor point 330, 330A a contact 282 of the circuit board 274 is disposed at a same location as the terminal end 200 of the flex circuit 196 routed through the hinge assembly 294, as discussed further below. The terminal end 200 can have a contact configured to engage the contact 282 to provide electrical connections between the circuit board 274 and other electrical components on of the smart spectacles assembly 100.

FIG. 12 shows that the flange 314 can have structures for supporting features facilitating charging of the battery 394. In one embodiment the flange 314 can have one or a plurality of charging contact passages 326 disposed therethrough. The charging contact passages 326 can be occupied by charge conductors 370 that can be exposed on the outside surface of the left temple 162. The charge conductors 370 disposed in the charging contact passage 326 can be exposed on the outside surface of the elongate body 270 of the left temple 162. Current can be caused to flow through charge conductors 370 disposed through the charging contact passage 326 to the terminal end 200 of the flex circuit 196 and thereby to the battery 394. The charge conductors 370 disposed on the left temple 162 can be configured to be the only charging contact of the smart spectacles assembly. In some embodiments, the charge conductors 370 can be disposed on both the left temple 162 and the right temple 166 to allow charging on either side of the smart spectacles assembly 100.

FIG. 12 also shows that the flange 314 can have one or a plurality of magnet apertures 322. The magnet apertures 322 are shown holding or peripherally enclosing a hinge magnet 366 in each of the magnet apertures 322. The hinge magnet 366 aid in securing the smart spectacles assembly 100 to a charging unit, which can include a power cord with a fixture or a charging base station. The power cord fixture or the charging base station can have magnetic features for attracting the hinge magnet 366 so that the smart spectacles assembly finds a charging position when placed adjacent to the charger.

FIG. 12 also shows that the hinge assembly 294 has a temple interface 334 that mechanically secures the elongate body 270 of the left temple 162 to the hinge assembly 294. The temple interface 334 includes a plurality of ridge projections 338. The ridge projections 338 extend around the periphery of a portion of the flange 314 adjacent to the barrel 306. The ridge projections 338 comprise at least one recess and at least one projection near the at least one recess. The ridge projections 338 are configured to mate with corresponding features in the blind recess 272 of the elongate body 270. The temple interface 334 also includes a peripheral flat 342 and a medial projection. The peripheral flat 342 is configured to abut the end face of the elongate body 270. The peripheral flat 342 extends along four edges around the flange 314 in one embodiment and allow for transferring loads between the elongate body 270 and the hinge assembly 294 in folding an unfolding the smart spectacles assembly 100. In the illustrated embodiment, the hinge assembly 294 includes a medial projection 346 configured for engagement with the elongate body 270 of the left temple 162. The medial projection 346 can be disposed only a medial side of the peripheral flat 342. The medial projection 346 provides enhanced load transfer in folding the smart spectacles assembly 100.

Figure 13:
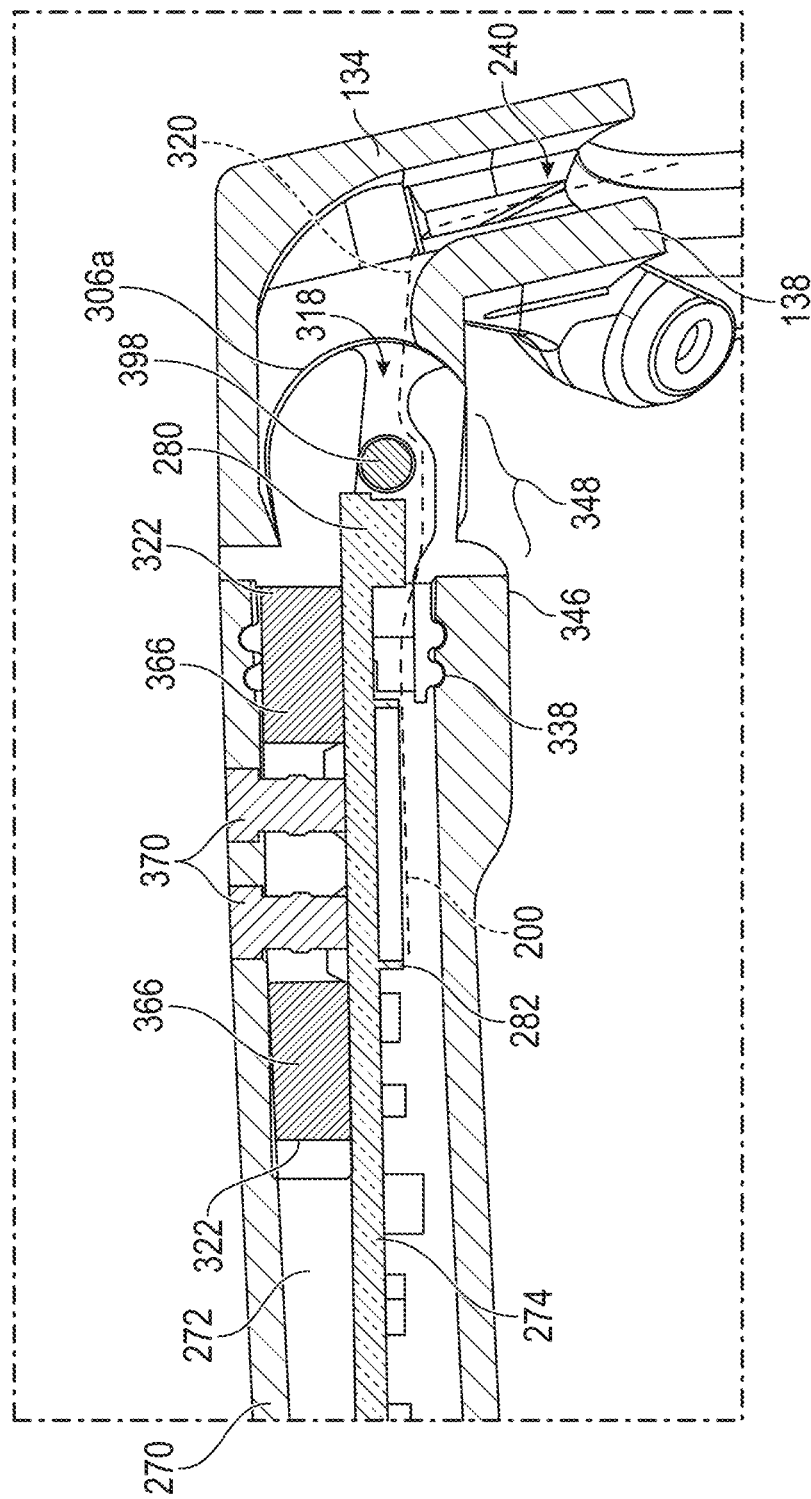
FIG. 13 shows a cross-sectional view of the smart spectacles frame assembly illustrating a flex cable routing path through the hinge assembly, the section taken at plane 13-13 in FIG. 2E.
Figure 14:
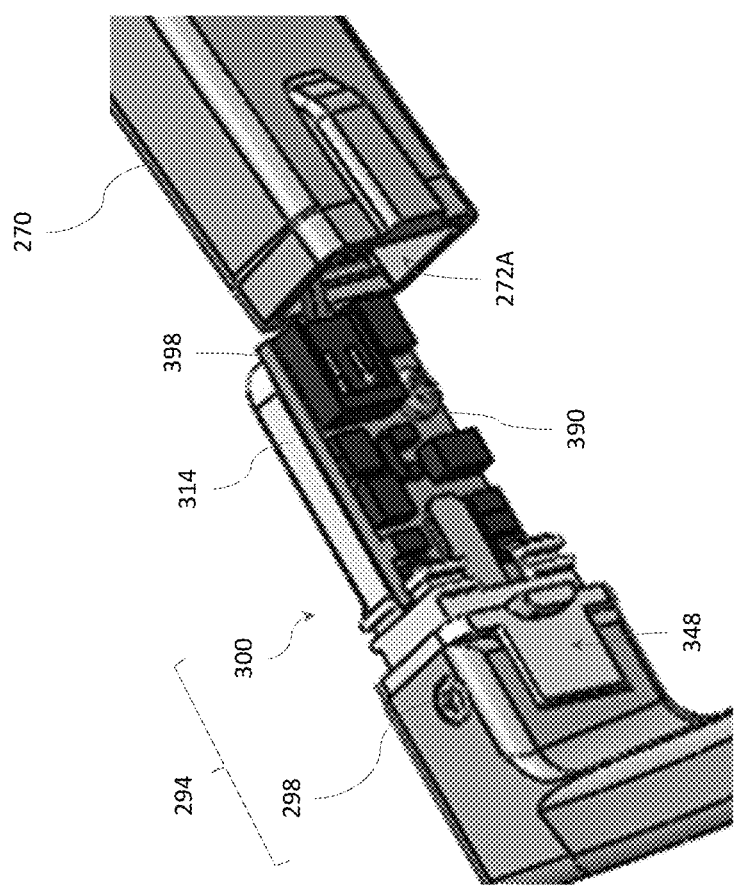
FIG. 14 is an exploded view of a right side of the smart spectacles frame assembly showing the right temple spaced apart from a circuit board configured to be disposed in the right temple.
Figure 15:
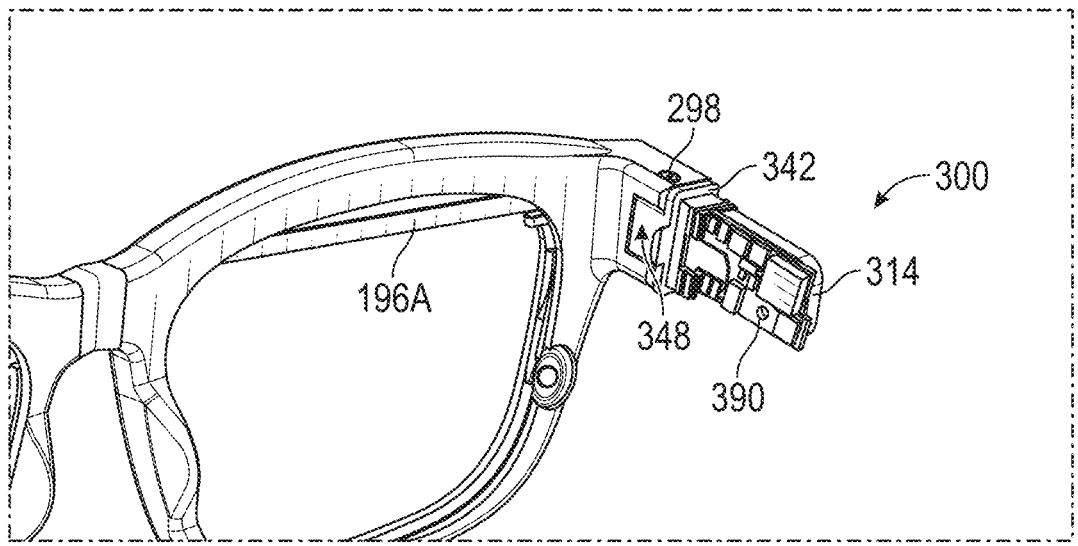
FIG. 15 is rear perspective view of a sub-assembly of the right side of the smart spectacles frame assembly, showing a circuit board coupled with a flex circuit of the smart spectacles frame assembly.

FIG. 13 shows many of the features hereinbefore described in greater clarity. The anterior segment 134 and the posterior segment 138 of the spectacles frame 116 extend laterally of the left rim 120A toward a hinge portion of the spectacles frame. The conductor passage 240 is disposed between the anterior segment 134 and the posterior segment 138 and continues into the hinge portion wherein a flex cable routing path 320 can be provided. The hinge portion of the spectacles frame 116 also has a passage in which the barrel 306 of the hinge assembly 294 is disposed and in which the barrel moves about the axle 298. The barrel 306 comprises a rounded surface 306A that moves or slides over curved edges of the spectacles frame 116. A translucent portion 348 of the hinge assembly 294 (e.g., a translucent hinge) is disposed on a medial side of the assembly seen in FIG. 13. A LED assembly 280 is disposed within the hinge assembly 294 in a passage disposed behind the translucent portion 348 such that light emitted by the LED assembly 280 can be directed and shine through the translucent material of the translucent portion 348 and be visible to the wearer. The LED assembly 280 can be mounted to an end of the circuit board 274 disposed adjacent to the barrel 306 in the assembly.

FIG. 13 shows that electrical connection between the circuit board 274 and other components, e.g., the camera 194, the sensor 214, and component in the right temple 166, can be made through the hinge assembly 294. A passage 318 is provided through the barrel 306 to allow the flex cable routing path 320 to continue from the spectacles frame 116, through the barrel 306 and into the blind recess 272 of the elongate body 270. The terminal end 200 of the flex circuit 196 can be secured to the contact 282 and positioned within the blind recess 272. A span of the flex circuit 196 adjacent to the terminal end 200 can be disposed between the LED assembly 280 and the translucent portion 348. The light emitted by the LED assembly 280 shines through and/or around the span of the flex circuit 196 such that the translucent portion 348 advantageously is uniformly illuminated rather than providing a more point source light output from the translucent portion 348 of the hinge assembly 294. A point source providing a very bright spot or hot spot through the translucent portion 348 would be a more distracting signal to the user than would be the diffuse light in the depicted embodiment. The connection between the hinge assembly 294 and the elongate body 270 can be seen as well. The ridge projections 338 of the hinge assembly 294 can engage ridges and recesses of the elongate body 270 in the blind recess 272. The peripheral flat 342 can engage an end face of the elongate body 270 when the left temple 162 is fully assembled. The charge conductors 370 can be seen having a free or exposed end on the lateral surface of the left temple 162 and an opposite end of the charge conductors 370 in contact with the circuit board 274. The charge conductors 370 can comprise, for example, electrically conductive metals or otherwise be metallic surfaces exposed on the lateral side of the left temple 162 configured to transmit an electrical charge between the circuit board 274 and a charging unit. Also, the hinge magnets 366 are disposed in the blind recess 272 of the elongate body 270 to provide for magnetic attraction of the smart spectacles assembly 100 to a charging base station or a fixture of a charging cord.

Figure 16:
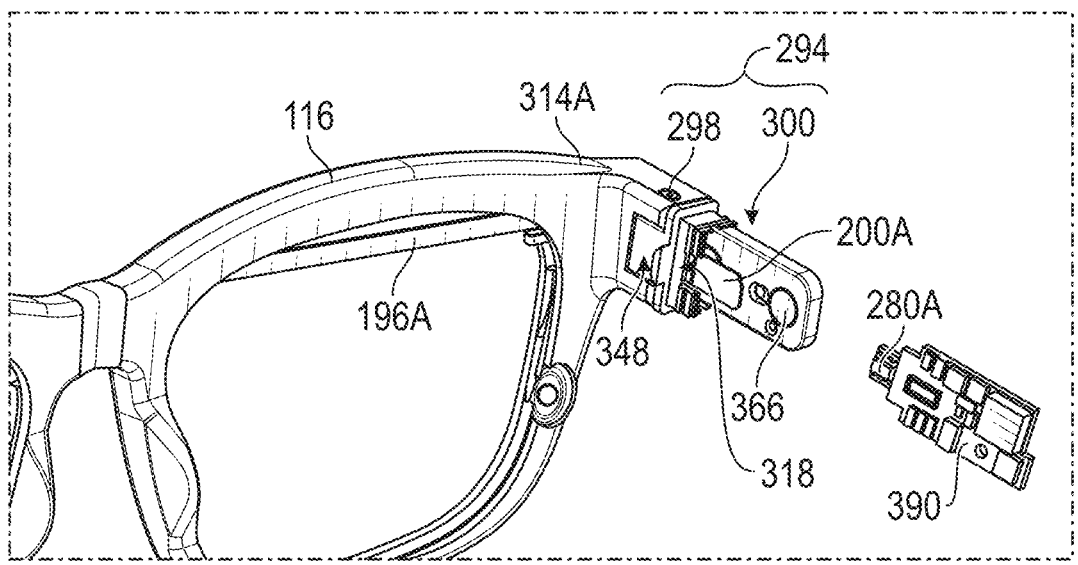
FIG. 16 is an exploded view of a sub-assembly of the right side of the smart spectacles frame assembly, showing a circuit board spaced apart from a hinge assembly configured to couple the right temple to the spectacles frame.

FIGS. 14-17 show aspects of an assembly of the right temple 166. The right temple 166 includes an elongate body 270 having a blind recess 272A. A hinge assembly 294 is provided that is coupled with a right side of the spectacles frame 116. The hinge assembly 294 is similar to the hinge assembly 294 coupled with the left temple 162, described above. The hinge assembly 294 includes an axle 298 coupled with a hinge portion of the right side of the spectacles frame 116. The hinge assembly 294 includes a rotatable member 300 having a flange 314 at one end and a barrel 306. As discussed above, a translucent portion 348 is provided on the medial side of the hinge assembly 294 disposed at the connection of the right temple 166 to the spectacles frame 116. The translucent portion 348 can be a unitary or monolithic translucent body, or can comprise multiple components which are mechanically or otherwise connected. The flange 314 is coupled with hinge magnets 366 and charge conductors 370 as discussed in connection with the hinge assembly 294 on the left temple 162. A circuit board 390 is coupled with a medial side of the flange 314 at an anchor point 330, e.g., using a screw. FIG. 16 shows that a flange 314A can be disposed on an opposite side of the frame 116 as is the flange 314. The circuit board 390 can be coupled to a conductor 398 in electrical communication with a battery 394 disposed in the blind recess 272 of the elongate body 270 of the right temple 166. FIG. 16 shows that the circuit board 390 also has a LED assembly 280A disposed on an end thereof. The end of the circuit board 390 with the LED assembly 280A is configured to be inserted through a passage 318 into the hinge assembly 294 to a position behind the translucent portion 348. As the LED assembly 280A is illuminated the light emitted thereby illuminates the translucent portion 348 in a manner visible in the peripheral vision of the wearer. This facilitates communication with the wearer using a lower power consumption approach.

Figure 17:
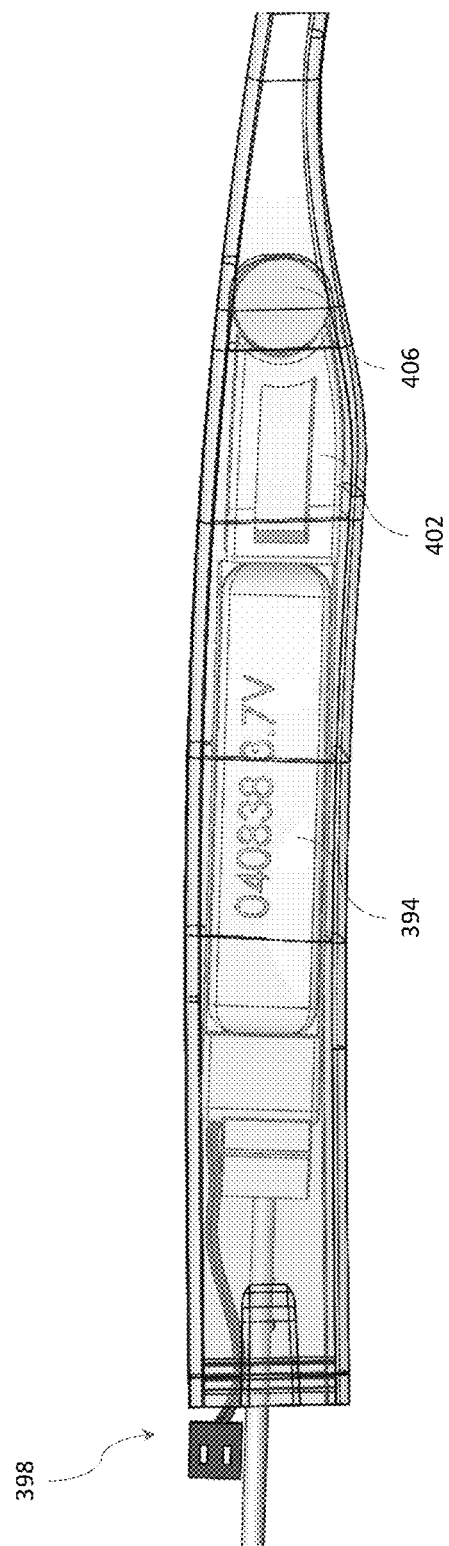
FIG. 17 is a side view of the right temple having a battery and a battery conductor disposed illustrating a method of assembling the components disposed in the right temple.

FIG. 17 shows one approach for positioning the battery 394 in the blind recess 272 of the elongate body 270 of the right temple 166. The battery 394 can be disposed in a middle section of the blind recess 272 by providing a battery spacer 402 having a first end configured to abut an end of the battery 394 disposed deepest in the blind recess 272 and a second end opposite the first end. The second end can be configured to contact an internal wall of the elongate body 270 or can be configured to mate with another component disposed in the blind recess 272. In the illustrated embodiment a temple magnet 406 is disposed in the blind recess 272. The temple magnet 406 can comprise a rare earth magnet or another magnet configured to generate a magnetic field that can be sensed by a magnetometer disposed on the smart spectacles assembly 100. For example, a magnetometer 284 can be disposed on the circuit board 274 as seen in FIG. 10. The magnetometer can be configured to generate a signal to the processor 278. The processor 278 can be configured to process the signal to determine whether the right temple 166 is folded out or is folded in against the spectacles frame 116 based on how the magnetometer 284 detects the magnetic fields generated by the temple magnet 406. Detection the folded state can enable the processor 278 to modulate components into a lower power consumption mode.

FIGS. 18A-18C illustrate a technique for routing conductors through the conductor passage 240 that enables small flex circuits to extend through narrow passages of the spectacles frame 116 while components located at ends may be too large to extend therethrough. For example, the portion of the conductor passage 240 extending through the bridge 122 can be much smaller than the camera 194 that is mounted on each side of the bridge 122, e.g., on the temporal span 130 of the left rim 120A and the temporal span 130 of the right rim 120B. The flex circuit 196 coupled with the camera 194 on the left side of the smart spectacles assembly 100 can have a bridge end having a first contact 202 that is sized to fit within the bridge 122. The flex circuit 196A coupled with the camera 194 on the right side of the smart spectacles assembly 100 can have a bridge end having a second contact 202A. The flex circuit 196A can extend to a terminal end 200A. In assembly the camera 194 for the left rim 120A can be positioned on the left side of the spectacles frame 116 and the camera 194 for the right rim 120B can be positioned on the right side of the spectacles frame 116. Thereafter the bridge end of the flex circuit 196 can be positioned through the bridge 122 and coupled with the second contact 202A at the bridge end of the flex circuit 196A. The joined flex circuits can be moved such that the first contact 202 and the second contact 202A are positioned in the bridge 122 after being connected together.

Figure 19:
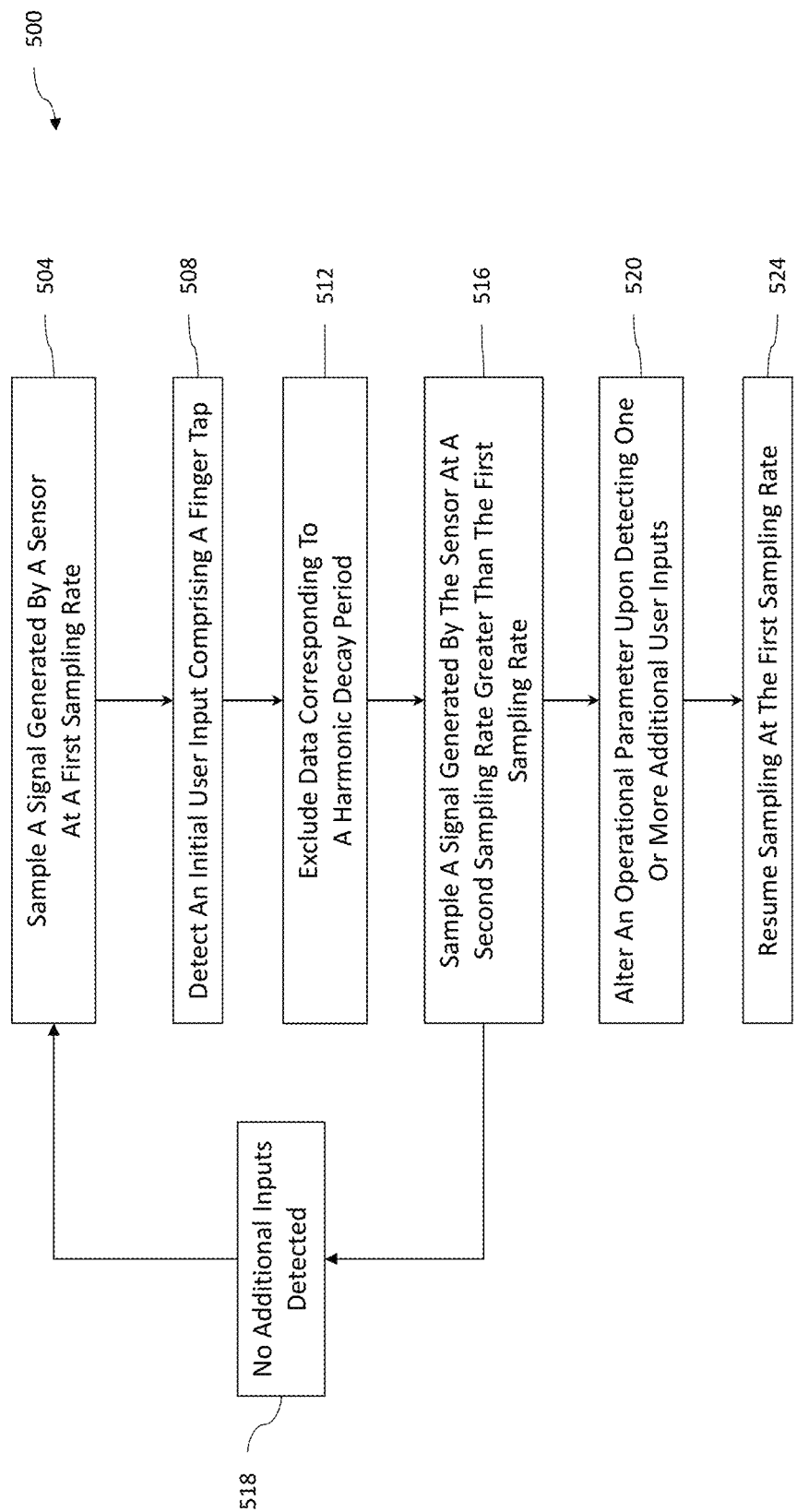
FIGS. 19-20 are flow charts illustrating processes by which a user can input system controls to a spectacles assembly such as that of FIG. 1.

The smart spectacles assembly 100 can handle a range of wearer inputs and interactions in various embodiments. FIG. 19 illustrates a control routine 500 which is one of many routines that can be provided by the processor 278. As discussed above the processor 278 is integrated into the smart spectacles assembly 100, e.g., mounted to the circuit board 274 and located in the left temple 162. In a step 504 the processor 278 samples a signal generated by the inertial measurement unit 410. In this context, the inertial measurement unit 410 is configured to detect tapping of a finger on the left temple 162 or elsewhere on the smart spectacles assembly 100, e.g., on the spectacles frame 116 or the right temple 166. For this reason, the inertial measurement unit 410 is acting as a finger tap sensor in this routine. The inertial measurement unit 410 has an accelerometer that can detect an acceleration that results from the tapping of the finger. The processor 278 preferably can operate in more than one power consumption mode. The processor 278 can operated in an ultralow power consumption configuration. In this configuration, the number of operations run by the processor is limited. As one example, the sampling rate of data from the inertial measurement unit 410 can be restricted in the ultralow power consumption configuration. The processor 278 can operate in a high performance configuration. The processor 278 can switch between the ultralow power consumption configuration and the high performance configuration depending on the data processing needs of the smart spectacles assembly 100.

In one example, the processor 278 samples a signal produced by the inertial measurement unit 410 at a first sampling rate. The first sampling rate is one that would detect a finger tap but is not so high a rate that the processor 278 might process a lot of signals not indicative of a user input (e.g., harmonic vibrations created by the initial finger tap, as explained herein). The first sampling rate can be below about 300 Hz, e.g., about 25 Hz, about 50 Hz, about 75 Hz, about 100 Hz, about 150 Hz, about 200 Hz, about 250 Hz, or a sampling rate within a range below any of the foregoing values or within a range including any of the foregoing values as end points of the range.

In a step 508, the processor 278 is configured to detect an input while sampling at the first sampling rate. The input can be an initial input of the wearer of the smart spectacles assembly 100 in a particular instance. The initial input can be a finger tap, as discussed above. The finger tap will be detected following an impact on the smart spectacles assembly 100 causing an acceleration, which would be detectable by an accelerometer on the inertial measurement unit 410. In other embodiments, a dedicated accelerometer could be provided in place of or in addition to the inertial measurement unit 410. In other instances, the initial input can be another form of tactile input, e.g., a swipe, touch, hold or a combination of these detectable by a capacitance sensor.

An accelerometer may continue to sense motion following an initial tap. The motion can be a harmonic isolation following the initial signal generated upon impact. As such, the processor 278 can be configured to exclude data corresponding to this period in which specious data may be produced. In some cases, the sensor output exhibits harmonic decay in the output and the processor 278 is configured to wait until the harmonic decay has progressed and/or the harmonic decay period has elapsed to where a signal that is sensed is not a continuation of the signal generated by the initial input. Thus, in a step 512 the control routine 500 excludes data corresponding to a harmonic delay period. The harmonic delay period can be pre-defined. The harmonic delay period can last for one hundred to three hundred milliseconds. The harmonic delay period can last for between about one hundred to about 500 milliseconds. In this context, excluding data can involve not sampling data produced by the inertial measurement unit 410 after the initial input is detected. In some cases, the processor 278 continues sampling data during this period but the data is not used for the purposes of detecting other inputs.

In a step 516, the processor 278 samples the signal generated by the inertial measurement unit 410 after the harmonic delay period has concluded. The sampling in step 516 can be at a second sampling rate. The second sampling rate can be greater than the first sampling rate. The second sampling rate can be two to four times greater than the first sampling rate. The second sampling rate can be about 100 Hz, about 150 Hz, about 200 Hz, about 250 Hz, about 300 Hz, or within a range including any of the foregoing values as endpoints. The step 516 can continue for a period during which a second tap in a two tap or multi-tap input would be expected. The period during which the second sampling rate can be applied is sometimes referred to herein as a heightened sampling rate period. The heightened sampling rate period can extend for about 100 milliseconds, about 200 milliseconds, about 300 milliseconds, about 400 milliseconds, about 500 milliseconds, about 600 milliseconds, or for a range of milliseconds including any of the foregoing values as endpoints, e.g., about 300 to about 500 milliseconds.

In one embodiment, the processor 278 processes the signal from the inertial measurement unit 410 to identify the harmonic delay period. For example, the output of the inertial measurement unit 410 can be monitored over a few hundred milliseconds to identify when the signal has fallen to fraction of the original amplitude of the signal such that a second or subsequent input would be clearly observed. The step 516 can commence at or after that point has been identified. Thus, the harmonic delay period need not necessarily be pre-defined. In this approach the processor 278 can dynamically delay the detection of second or subsequent inputs (e.g., taps) on the smart spectacles assembly 100. In a pre-defined fixed harmonic delay period approach the processor 278 can delay detection until after the fixed period has passed.

The step 516 can conclude with the detection of one or more additional inputs. The processor 278 is configured to interpret two taps as a user input to the system. In that case, the processor 278 proceeds to a step 520 in which an operational parameter of the smart spectacles assembly 100 is altered, as discussed below. If the processor 278 does not detect one or more additional user inputs, then in a step 518 the processor 278 concludes that no additional taps have been received. The processor 278 concludes that no additional taps have occurred. The processor 278 proceeds from the step 518 to the step 504 in which the processor 278 resumes sampling the signal from the inertial measurement unit 410. The resumed sampling can be at the first sampling rate or at another rate lower than the second sampling rate. In one embodiment, the step 518 directs the smart spectacles assembly 100 to revert to an ultralow power consumption mode as a precursor to the step 504. For example, the processor 278 could revert to an ultralow power consumption mode until a user input is received, e.g., a first finger tap could cause the control routine 500 to commence the step 504. In the event no additional input is detected in the first heightened sampling rate period the step 516 can repeat one or more additional heightened sampling rate periods, e.g., two, three or four additional heightened sampling rate periods, before the step 518 occurs.

If in the step 516 one or more additional user inputs is received, then in a step 520 an operational parameter of the smart spectacles assembly 100 can be altered. The time period from before the step 508 to the detecting of the additional input(s) in the or before the step 520 can be about a second or less in some embodiments. The step 520 in which the operational parameter is altered can be carried out after a harmonic delay period concludes, and thereafter following detection of additional inputs. The step 520 in which the operational parameter is altered can be carried out at a heightened sampling rate.

The step 520 in which an operational parameter of the smart spectacles assembly 100 can be altered can have many variations. In one case, the step 520 provides for altering the operational parameter by generating a signal to be sent to a device that a notification can be dismissed. Notifications of various kinds can be generated by or with the smart spectacles assembly 100 or by or with a connected smartphone or other mobile device or computer connected by the communications interface 88 and through the Wi-Fi and/or Bluetooth device 86 to the processor 278. As discussed above, the smart spectacles assembly 100 can communicate with the wearer by way of the translucent portion 348 of the hinge assembly 294. In one mode, the smart spectacles assembly 100 flashes light visible to the eye of the wearer as a notification. The step 520 can alter this behavior by generating a signal to be sent to a circuit in the processor 278 to stop the flashing light. In another mode, the smart spectacles assembly 100 can be networked with another device, such as a remote computer, a mobile device, a smartphone, a server, e.g., by way of the communications interface 88 and through the Wi-Fi and/or Bluetooth device 86. The step 520 can alter an operational parameter by generating a signal to be sent to the mobile device that a notification on the device can be dismissed. Thus, the wearer can dismiss a notification that would otherwise be presented to the wearer or to a healthcare professional in control of a device networked with the smart spectacles assembly 100.

In another mode, the step 520 can alter an operational parameter by controlling data gathering or logging of various kinds. As one technique for controlling battery life, the smart spectacles assembly 100 can be configured to periodically cease or otherwise pause high level operations such as data logging or image capture. The step 520 can alter these operational parameters by causing the smart spectacles assembly 100 to exit or enter a battery conserving behavior and commence or cease, respectively, logging data. The step 520 can alter an operational parameter corresponding to an inactive state even when battery conservation is not at issue. The step 520 can cause the smart spectacles assembly 100 commence or otherwise begin logging data following an inactive period, which may be selected by the user by a user input detected using the control routine 500. In another mode, the step 520 can alter an operational parameter by generating a signal to be sent to a device that a notification can be temporarily dismissed, or to have the notification return after a set period of time. If this altering of the operational parameter is performed, then the notification which was generated by or with the smart spectacles assembly 100 could be dismissed and re-issued after a set snooze time. A snooze time can las for a few, e.g., five, minutes, at which time the temporarily dismissed notification could be re-communicated to the user, by way of the translucent portion 348 of the hinge assembly 294, or by other means. Although one great advantage of the smart spectacles assembly 100 is the ability to more carefully monitor a wearer's compliance with a treatment regimen (e.g., the occurrence of a medical compliance event), there may be times when the wearer is unable to immediately address the issued notification by the smart spectacles assembly 100. For example, if the user's hands are occupied at a time when a notification is issued to remind the user to apply eyedrops. There can be diverse reasons for temporarily dismissing a notification by the smart spectacles assembly 100. Regardless of the reason, the control routine 500 can be used to alter the operational parameters of the smart spectacles assembly 100 by causing the spectacles assembly to temporarily dismiss a notification.

An example of an inactive state can include a state in which image capture has been intentionally stopped. Although one great advantage of the smart spectacles assembly 100 is the ability to capture, store and provide for later analysis a stream of images there may be times when the wearer is wearing the smart spectacles assembly 100 for vision correction but prefers not to capture images. There can be diverse reasons for the wearer implementing the inactive period during which images capture is stopped but regardless of the reason, the control routine 500 can be used to alter the operational parameters of the smart spectacles assembly 100 by causing the spectacles assembly to cease image capture in an inactive state. The wearer can tap on any part of the smart spectacles assembly 100, e.g., the left temple 162 or the right temple 166 which can be detected by the processor 278 processing the signals of the inertial measurement unit 410. The tap input can be detected at the step 508 and at the step 520.

As discussed above, the control routine 500 can thereafter be used to resume image (or other data) capture following an inactive period. Following a tap input to alter an operational parameter to cause the smart spectacles assembly 100 to implement an inactive period, a step 524 can be implemented in which sampling of data at the first sampling rate can resume. The step 524 can return the control routine 500 to the step 504. If the smart spectacles assembly 100 is in an inactive state, a tap input detected at the step 508 can be confirmed in the step 520 where a second or subsequent user input (e.g., another tap) can be detected and an operational parameter of the smart spectacles assembly 100 altered. The smart spectacles assembly 100 can enter into an active period, in which data is logged and/or images are captured. In another mode, the step 520 could alter an operational parameter to cause the smart spectacles assembly 100 to implement an inactive period for only a predetermined period of time, such that the control routine 500 could enter the smart spectacles assembly 100 into an inactive period for a set period of time, after which the smart spectacles assembly 100 returns or enters into an active period without requiring user input.

Figure 20:
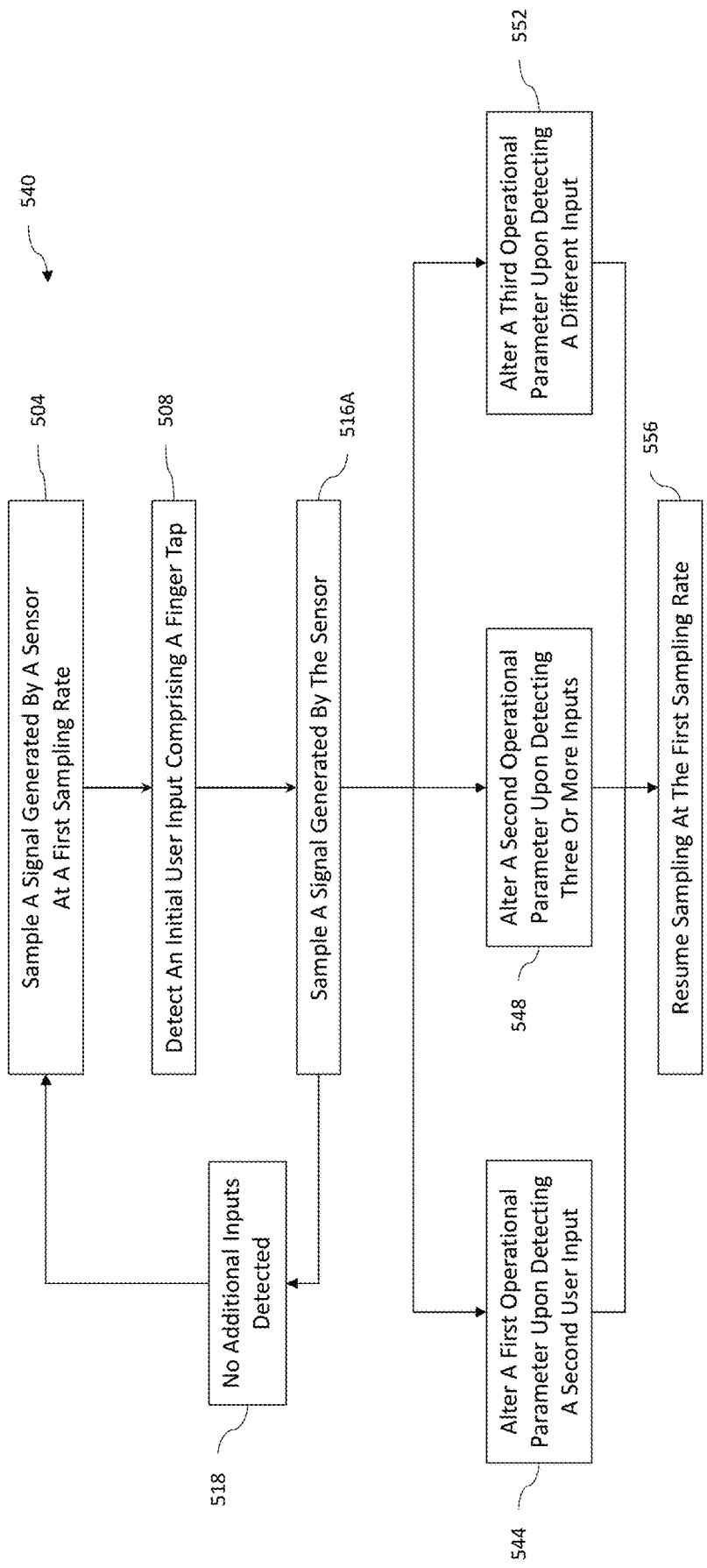

FIG. 20 illustrates another control routine 540 which is one of many routines that can be provided by the processor 278. As discussed above the processor 278 is integrated into the smart spectacles assembly 100, e.g., mounted to the circuit board 274 and located in the left temple 162. The steps within control routine 540 are substantially similar to the steps within control routine 500, unless elaborated otherwise. The step performed after step 516A can vary based on the number or type of user inputs received after a harmonic delay period concludes. In step 544, if step 516A concludes with detecting a second user input, then a first operational parameter can be altered. In step 548, if step 516A concludes with detecting three or more user inputs, then a second operational parameter can be altered. In step 552, if step 516A concludes with detecting another form of user input following detecting the initial user input, then a third operational parameter can be altered. The step 552 can include an input on an opposite temple or other portion of the smart spectacles assembly 100 than through which the initial user input was received. These other forms of user input, e.g., a swipe, touch, hold or a combination of these, can be detectable by the same or a different sensor used to detect the initial user input. For example, a capacitance sensor within the smart spectacles assembly 100 can detect a swipe input. The operational parameters could be ordered such that the first operational parameter within step 544 is more frequently needed than the second operational parameter within step 548. In this way a simpler input (e.g., two taps versus three taps) is used to achieve the more frequent operational parameter adjustment. Following an alteration of an operational parameter, such as to cause the smart spectacles assembly 100 to implement an inactive period or otherwise, a step 556 can be implemented in which sampling of data at the first sampling rate can resume. The step 556 can return the control routine 540 to the step 504. Additional steps not shown can be performed following the step 516A leading to the step 556, such as altering a fourth operational parameter upon detecting a fourth input, or so on, to further increase the possible number of specific user inputs which could correlate to a modification of an operational parameter.

As discussed above, the smart spectacles assembly 100 can provide generally uninterrupted stream of image data regarding the eyes of the wearer. As such, user implemented inactive periods should continue only so long as intended. Accordingly, the smart spectacles assembly 100 can implement a notification to remind the wearer to resume image capture as soon as possible. The step 524 can be performed at the same time as or can precede by pre-defined period the smart spectacles assembly 100 issuing a notification on the smart spectacles assembly 100 or on a networked device. The pre-defined period can be a pre-defined non-imaging period. The notification can be a reminder to use the control routine 500 (or another control pathway) to resume recording images. The notification can be by the translucent portion 348 of the hinge assembly 294 if the notification is issued by the smart spectacles assembly 100. The notification can by on a user interface of a smartphone or other mobile device or computer connected by the communications interface 88 to the processor 278.

The control routine 500 can be used to augment the information collated with images generated in an image stream by the smart spectacles assembly 100. The control routine 500 can be used to alter the operational parameter of the smart spectacles assembly 100 by causing the spectacles assembly to generate a signal causing the smart spectacles assembly 100 or another device to add a notation to a data point, such as an image or time period, or to record a notation that can be associated with a data point. A wide variety of notations could be associated with an image or time period. In one embodiment, a notation can pertain to a physical condition of the wearer. The physical condition can include the wearer suffering from or otherwise experiencing a migraine or less serious headache. The notation can indicate that the wearer has taken an action relevant to a health condition, e.g., that the wearer has taken eyedrops or other medicine. Notations could also be made to correspond to a time period, rather than with an image. This can be beneficial if the user wishes to create a notation when images are not being captured. The user could create a notation that they have taken an eyedrop, which would be beneficial when performing image capture at a later time. The physical condition can include the wearer suffering from symptoms consistent with or being exposed to environmental conditions exacerbating a dry eye condition. In one case, the control routine 500 can be used by the wearer to cause the smart spectacles assembly 100 to generate a signal to cause the smart spectacles assembly 100 or another device to add a notation to currently logged data of the wearer starting or stopping viewing a computer screen, television, or mobile device interface. The control routine 500 can be used to enable the smart spectacles assembly 100 or another device to calculate screen time usage, e.g., by commencing an algorithm configured to observe the presence of the reflection 48 in the imaging area IA (see FIG. 5A), an algorithm configured determine screen distance based upon the size, shape, or position of the reflection 48, or both the duration and the distance based on the observation of the reflection 48.

The control routine 500 can be used to alter an operational parameter related to data transfer from the smart spectacles assembly 100 to another device. The control routine 500 can be used to detect an initial input at the step 508 and a confirmatory input at the step 520 confirming an intent of the wearer to transfer data from memory on the smart spectacles assembly 100 to memory in an external device. The control routine 500 can alter an operational parameter of the smart spectacles assembly 100 by causing the communications interface 88 to activate to send data by way of the Wi-Fi and/or Bluetooth device 86. The data can be collected on the cloud 80 or another external computer in a local network or accessible by the Internet.

There are many possible variations on the control routine 500 shown in FIG. 19. For example, the step 512 may not be required if the smart spectacles assembly 100 is configured to analyze the signal of the inertial measurement unit 410 to differentiate between a second or subsequent tap input and transient decay signals. Also, in some cases a user input is so distinct the step 508 is sufficient for the smart spectacles assembly 100 to confirm that the wearer intends an alteration in an operational parameter of the smart spectacles assembly 100. For example, the processor 278 can be configured to process the signal of the inertial measurement unit 410 to differentiate background forces from a user input tap, e.g., by setting a background force threshold below which no user input tap is deemed to have been occurred but above which the user input tap is considered to have occurred. The processor 278 could also consider the direction of the force represented by the signal generated by the inertial measurement unit 410. A force toward the head of the wearer could be interpreted to correspond to a user input tap whereas a force directed from the head outward would not be so interpreted. Thus, in these approaches, the control routine 500 could proceed from the step 508 directly to altering the operational parameter as in the step 520 without waiting for one or more additional inputs.

The step 524 may or may not occur if the control routine 500 is used to cause the smart spectacles assembly 100 to cease operating or to operate with functions less than or not including sampling for user input taps. This can occur if or when the smart spectacles assembly 100 are folded with the left temple 162 and the right temple 166 folded up against the spectacles frame 116. In this state, no user inputs are expected or meaningful. There is no need for the control routine 500 to resume sampling in step 524. Many other possibilities exist for combining some and not all of the steps of the control routine 500 illustrated in FIG. 19.

Features, materials, characteristics, or groups described in conjunction with a particular aspect, implementation, or example are to be understood to be applicable to any other aspect, implementation or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing implementations. The protection extends to any novel one, or any novel combination, of the features disclosed in this specification (including any accompanying claims, abstract and drawings), or to any novel one, or any novel combination, of the steps of any method or process so disclosed.

While certain implementations have been described, these implementations have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some implementations, the actual steps taken in the processes illustrated or disclosed may differ from those shown in the figures. Depending on the implementation, certain of the steps described above may be removed, others may be added. For example, the actual steps or order of steps taken in the disclosed processes may differ from those shown in the figure. Depending on the implementation, certain of the steps described above may be removed, others may be added. Furthermore, the features and attributes of the specific implementations disclosed above may be combined in different ways to form additional implementations, all of which fall within the scope of the present disclosure.

Although the present disclosure includes certain implementations, examples and applications, it will be understood by those skilled in the art that the present disclosure extends beyond the specifically disclosed implementations to other alternative implementations or uses and obvious modifications and equivalents thereof, including implementations which do not provide all of the features and advantages set forth herein. Accordingly, the scope of the present disclosure is not intended to be limited by the described implementations, and may be defined by claims as presented herein or as presented in the future.

Conditional language, such as "can," "could," "might," or "may," unless specifically stated otherwise, or otherwise understood within the context as used, is generally intended to convey that certain implementations include, while other implementations do not include, certain features, elements, or steps. Thus, such conditional language is not generally intended to imply that features, elements, or steps are in any way required for one or more implementations or that one or more implementations necessarily include logic for deciding, with or without user input or prompting, whether these features, elements, or steps are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise, the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

What is claimed is:

1. An ophthalmic monitoring system, comprising:
    an eyeglasses frame comprising a left rim and a right rim, each of the left rim and the right rim comprising an anterior segment having an anterior lens mounting edge, a posterior segment having a posterior lens mounting edge, and a lateral span comprising a u-shaped inner periphery extending from the anterior lens mounting edge to the posterior lens mounting edge;
    an image sensor/camera enclosure disposed on the lateral span of each of the posterior segment of the left rim and the posterior segment of the right rim, the image sensor/camera enclosure disposed about a space interior to the eyeglasses frame extending from a first end adjacent to the anterior lens mounting edge to a second end disposed posterior of the posterior segment of the left rim and of the right rim, the second end comprising an observation aperture, wherein an image viewing axis perpendicular to the first end and to the observation aperture is angled medially and at an angle α between 25 degrees and 40 degrees relative to a vertical plane extending in a medial-lateral direction and upwardly at an angle β between 10 degrees and 25 degrees relative to a horizontal plane;
    a sensor window disposed through the posterior segment of the right rim or the posterior segment of the left rim, the sensor window facing posteriorly toward a wearer of the eyeglasses frame and being disposed between the camera enclosure and a hinge assembly coupled with the lateral span;
    a camera assembly comprising an image sensor/camera disposed in the space interior to the eyeglasses frame adjacent to the observation aperture of the image sensor/camera enclosure and a conductor configured to convey image signals from and control signals to the image sensor/camera, the conductor disposed in the u-shaped inner periphery peripherally of the anterior lens mounting edge and the posterior lens mounting edge and extending in the u-shaped inner periphery from the image sensor/camera enclosure to the hinge assembly of the eyeglasses frame; and
    an ambient light sensor disposed adjacent to the sensor window, the ambient light sensor configured to capture light reflections from an imaging area including an eye of the wearer, the ophthalmic monitoring system configured to record information pertinent to ocular health of the wearer based on signals from the ambient light sensor.

2. The ophthalmic monitoring system of claim 1, wherein the observation aperture is angled medially and at an angle of between about 30 degrees and about 35 degrees and upwardly at an angle of between about 13 degrees and about 22 degrees.

3. The ophthalmic monitoring system of claim 1, wherein the sensor window is disposed through the posterior segment of the left rim or the posterior segment of the right rim.

4. The ophthalmic monitoring system of claim 1, further comprising a temperature sensor disposed on or in the eyeglasses frame.

5. The ophthalmic monitoring system of claim 1, wherein the ambient light sensor disposed adjacent to the ambient light sensor window comprises an IR sensor.

6. The ophthalmic monitoring system of claim 5, further comprising a flex circuit, wherein the conductor is a first conductor and further comprising a second conductor configured to convey signals from the IR sensor, the first conductor and the second conductor disposed in the flex circuit, at least a portion of the flex circuit disposed in the u-shaped inner periphery.

7. The ophthalmic monitoring system of claim 1, further comprising an IR sensor coupled with the eyeglasses frame and configured to sense infrared light reflected from an eye over which the eyeglasses frame is placed.

8. The ophthalmic monitoring system of claim 7, wherein the IR sensor comprises a single pixel infrared-sensitive light detector.

9. The ophthalmic monitoring system of claim 1, further comprising:
a right temple coupled with the right rim;
a left temple coupled with the left rim;
one of the right temple and the left temple comprising a blind recess having a first end of a circuit board assembly disposed therein, the first end of the circuit board having a processor mounted thereon, a second end of the circuit board assembly having an LED assembly disposed thereon; and
a hinge assembly connecting the left temple to the eyeglasses frame, the hinge assembly comprising:
an axle coupled with one or more mount points of the eyeglasses frame; and
a rotatable body comprising a barrel disposed at a first end and disposed around the axle, a flange at a second end opposite the first end, a temple interface forming a mechanical connection about a periphery of the blind recess of the left temple, a translucent portion disposed between the temple interface and the barrel, and a hinge passage disposed through the temple interface;
wherein the second end of the circuit board assembly is disposed in the hinge passage and through the temple interface such that the LED assembly is disposed at or adjacent to the translucent portion of the rotatable body such that light from the LED assembly is visible at the translucent portion.

10. An ophthalmic monitoring system, comprising:
an eyeglasses frame comprising a left rim and a right rim, the left rim and the right rim being coupled at a medial portion of the eyeglasses frame, each of the left rim and the right rim comprising a u-shaped inner periphery and a lens mounting edge between an anterior surface of an anterior segment of each of the right rim and the left rim and a posterior surface of a posterior segment of each of the right rim and the left rim;
a camera enclosure projecting along a viewing axis from a lateral span of the posterior segment of one of the left rim and the right rim, the camera enclosure defining an elongate space interior to the eyeglasses frame extending from an end comprising an observation aperture to another end opposite to the observation aperture, the elongate space being open on a medial side and enclosed by the eyeglasses frame on a lateral side, the observation aperture configured such that the viewing axis is angled medially and upwardly;
a camera assembly comprising a camera and a conductor configured to convey signals between the camera and a processor, the conductor routed through the u-shaped inner periphery from the camera enclosure to a hinge assembly coupling the eyeglasses frame to a temple, the camera disposed adjacent to the observation aperture, the camera oriented along the viewing axis to capture images of, over, and/or around a lateral side of an eye and surrounding tissue medially from a lateral canthus of the eye and from a lower eyelid of the eye to an upper eyelid; and
an ambient light sensor disposed in the lateral span at a location above the camera enclosure and positioned to view, through a sensor window formed at a location above the camera enclosure, the ambient light sensor detecting reflections from within an imaging area including an eye and skin surface of a wearer.

11. The ophthalmic monitoring system of claim 10, further comprising a temperature sensor.

12. The ophthalmic monitoring system of claim 10, wherein the sensor window is a first sensor window disposed on the posterior segment of the left rim, the eyeglasses frame comprising a second sensor window disposed on the right rim.

13. The ophthalmic monitoring system of claim 12, further comprising a temperature sensor is disposed adjacent to the second sensor window.

14. The ophthalmic monitoring system of claim 10, wherein the camera is oriented along the viewing axis to capture images of a non-anatomical object disposed on, over, or around the eye.

15. The ophthalmic monitoring system of claim 14, wherein the camera is oriented along the viewing axis to capture images of a patch disposed over the eye.

16. The ophthalmic monitoring system of claim 10, wherein the right rim and the left rim each comprise a hinge mount feature and wherein the hinge assembly comprises:
a first end coupled with or disposed at the hinge mount feature;
a second end coupled with the temple;
a translucent portion disposed along a medial side of the hinge assembly between the first end and the second end; and
an LED disposed adjacent to the translucent portion to illuminate the translucent portion within a field of view of the wearer of the ophthalmic monitoring system.

17. The ophthalmic monitoring system of claim 16, wherein the temple comprises a recess formed therein at an end coupled with the second end of the hinge assembly, and further comprising a circuit board disposed in the recess, the circuit board having a processor disposed thereon, and a conveyance extending from the circuit board through a hinge passage to electrically connect the processor to the LED disposed adjacent to the translucent portion.

18. An eyeglasses frame, comprising:
a left rim, a right rim, each of the left rim and the right rim comprising a medial side and a lateral side, the lateral side of one of the left rim and the right rim comprising a lens mounting edge and a blind recess extending from the lens mounting edge to a hinge assembly coupled with the lateral side;
a camera enclosure disposed on a posterior segment of the lateral side of one of the left rim and the right rim, the camera enclosure extending from a first end adjacent to the lens mounting edge to a second end disposed posterior of the posterior segment of the one of the left rim and the right rim, the second end of the camera enclosure comprising an observation aperture, wherein an image viewing axis disposed through the observation aperture is angled medially and upwardly toward an eye of a wearer when the eyeglasses frame is worn; and a sensor window disposed on the posterior segment of the lateral side of the same one of the left rim and the right rim upon which the camera enclosure is disposed, the lateral side configured to house an ambient light sensor to be oriented posteriorly through the sensor window to detect ambient light reflections from within an imaging area including the eye of the wearer toward which the image viewing axis is directed.

19. The eyeglasses frame of claim 18, wherein the blind recess is configured for routing a flex circuit coupled with an image sensor mounted in the camera enclosure.

20. The eyeglasses frame of claim 18, wherein the blind recess is disposed between the lens mounting edge and a peripheral wall of the eyeglasses frame.

21. The eyeglasses frame of claim 18, wherein the camera enclosure is disposed on the left rim and further comprising a second camera enclosure disposed on the lateral side of the right rim, the sensor window comprising a first environmental sensor window disposed on the left rim and further comprising a second sensor window disposed on the right rim.

* * * * *